United States Patent
Kochi et al.

(10) Patent No.: US 7,935,335 B2
(45) Date of Patent: May 3, 2011

(54) STRAINS BELONGING TO THE GENUS PAENIBACILLUS AND METHOD OF CONTROLLING PLANT DISEASE BY USING THESE STRAINS OR CULTURE THEREOF

(75) Inventors: Shinichiro Kochi, Tokyo (JP); Tsukasa Fujimaki, Tokyo (JP); Yoshinori Kanai, Fujieda (JP); Katsuyuki Futamata, Fujieda (JP); Yuzo Kioka, Tsuchiura (JP); Katsunori Noguchi, Tokyo (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 855 days.

(21) Appl. No.: 11/659,699

(22) PCT Filed: Aug. 8, 2005

(86) PCT No.: PCT/JP2005/014524
§ 371 (c)(1),
(2), (4) Date: Feb. 8, 2007

(87) PCT Pub. No.: WO2006/016558
PCT Pub. Date: Feb. 16, 2006

(65) Prior Publication Data
US 2007/0248583 A1  Oct. 25, 2007

(30) Foreign Application Priority Data
Aug. 9, 2004 (JP) .................... 2004-231858

(51) Int. Cl.
*A01N 63/00* (2006.01)
*A01N 65/00* (2006.01)
*C12N 1/00* (2006.01)
*C12N 1/20* (2006.01)

(52) U.S. Cl. ............... 424/93.46; 424/93.4; 424/93.1; 435/243; 435/252.1; 435/252.5

(58) Field of Classification Search .............. 424/93.46
See application file for complete search history.

(56) References Cited

U.S. PATENT DOCUMENTS
6,602,500 B1   8/2003   Kharbanda et al.

FOREIGN PATENT DOCUMENTS
| JP | 2-275898 A | 11/1990 |
| JP | 5-051397 A | 3/1993 |
| JP | 2000-502250 A | 2/2000 |

OTHER PUBLICATIONS

Kuroda et al., Heterocycles, 2000, 53:1533-1549; CAPLUS abstract only cited, accession No. 2000:499839.*

(Continued)

*Primary Examiner* — Ruth A Davis
*Assistant Examiner* — Sheridan R Macauley
(74) *Attorney, Agent, or Firm* — Sughrue Mion, PLLC

(57) ABSTRACT

Novel strains *Paenibacillus* sp. BS-0048, *Paenibacillus* sp. BS-0074, *Paenibacillus polymyxa* BS-0105 and *Paenibacillus* sp. BS-0277 and Fusaricidin A, Fusaricidin B and novel compounds 3 and 4 produced thereby have an activity of inducing resistance to plant diseases. Thus, they can protect plants from infections with fungi, bacteria, viruses and so on and, as a result, effectively control plant diseases.

13 Claims, 2 Drawing Sheets

OTHER PUBLICATIONS

Fukai et al., Tennen Yuki Kagobutsu Toronkai Koen Yoshishu, 1998, 40:461-466; CAPLUS abstract only cited, accession No. 1999:313207.*

Kajimura et al., Antibiotics, 1997, 50:220-228; CAPLUS abstract only cited, accession No. 1997:253474.*

Beatty, P.H. et al., "*Paenibacillus polymyxa* produces fusaricidin-type antifungal antibiotics active Against *Leptoshpaeria maculans*, the causative agent of blackleg disease of canola," Can. J. Microbiol., 2002, p. 159-169, vol. 48, No. 2.

Ko Kaneda, "Shinki Koshinkin Kosei Busshitsu Bacillopeptins oyobi Fusaricidins ni Tsuite", Journal of The Pharmaceutical Society of Japan, 2002, p. 651-671, vol. 122, No. 9.

Kajimura, Y. et al., Fusaricidins B, C and D, new depsipeptide antibiotics produced by *Bacillus polymyxa* KT-8: isolation, structure elucidation and biological activity, J. Antibiot. (Tokyo), 1997, p. 220-228, vol. 50, No. 3.

Kajimura Y. et al., Fusaricidin A, a new depsipeptide antibiotic produced by *Bacillus polymyxa* KT-8 Taxonomy, fermentation, isolation, structure elucidation and biological activity, J. Antibiot. (Tokyo), 1996, p. 129-135, vol. 49, No. 2.

S. Timmusk, Mechanism of Action of the Plant Growth Promoting Bacterium *Paenibacillus polymyxa*, Comprehensive Summaries of Uppsala Dissertations from the Faculty of Science and Technology, Dec. 4, 2003, pp. 1-40, Uppsala, Sweden.

W-J. Jung, et al., "Inoculation of *Paenibacillus illinoisensis* alleviates root mortality, activates of lignification-related enzymes, and induction of the isozymes in pepper plants infected by *Phytophthora capsici*", Biological Control, vol. 30, 2004, pp. 645-652.

S. Timmusk, et al., "The Plant-Growth-Promoting Rhizobacterium *Paenibacillus polymyxa* Induces Changes in *Arabidopsis thaliana* Gene Expression: A Possible Connection Between Biotic and Abiotic Stress Responses", The American Phytopathological Society, MPMI vol. 12, No. 11, 1999, pp. 951-959., Publication No. M-1999-0830-01R, Swedish University of Ag. Sciences, Uppsala, Sweden.

J. Dijksterhuis, "Antibiosis plays a role in the context of direct interaction during antagonism of *Paenibacillus polymyxa* towards *Fusarium oxysporum*", Journal of Applied Microbiology, vol. 86, 1999, pp. 13-21, Wageningen, The Netherlands.

X.Y. Liang, et al., "Control of damping-off of safflower by bacterial seed treatment", Canadian Journal of Plant Pathology, vol. 18, 1996, pp. 43-49, Alberta, Canada.

P. Nielsen, et al., "Multi-target and medium-independent fungal antagonism by hydrolytic enzymes in *Paenibacillus polymyxa* and *Bacillus pumilus* strains from barley rhizosphere", FEMS Microbiology Ecology, vol. 22, 1997, pp. 183-192, Published by Elsevier Science B.V., Copenhagen, Denmark.

A. S. Rosado, et al., "Production of a potentially novel anti-microbial substance by *Bacillus polymyxa*", World Journal or Microbiology and Biotechnology, vol. 9, 1993, pp. 521-528, Rio de Janeiro, Brazil.

P. Mavingui, et al., "In Vitro Chitinase and Antifungal Activity of a Soil, Rhizosphere and Rhizoplane Population of *Bacillus polymyxa*", Soil Biol. Biochem., vol. 26, No. 6, 1994, pp. 801-803, Great Britain.

P. Beatty, et al., "*Paenibacillus polymyxa* produces fusaricidin-type antifungal antibiotics active against *Leptosphaeria maculans*, the causative agent of blackleg disease of canola", Can. J. Microbiol., vol. 48, 2002, pp. 159-169, Edmonton, Canada.

Y. Kajimura, et al., "Fusaricidins B, C and D, new depsipeptide antibiotics produced by *Bacillus polymyxa* KT-8: isolation, structure elucidation and biological activity," Journal of Antibiotics, Mar. 1997, pp. 220-228, vol. 50, No. 3, Hiroshima, Japan.

Y. Kajimura, et al., "Fusaricidin A, a New Depsipeptide Antibiotic Produced by *Bacillus polymyxa* KT-8 Taxonomy, Fermentation, Isolation, Structure Elucidation and Biological Activity", Journal of Antibiotics, Feb. 1996, pp. 129-135, vol. 49, No. 2, Hiroshima, Japan.

S. Timmusk et al, "The Plant-Growth-Promoting Rhizobacterium *Paenibacillus polymyxa* Induces Changes in *Arabidopsis thaliana* Gene Expression: A Possible Connection Between Biotic and Abiotic Stress Responses," MPMI, vol. 12, No. 11, pp. 951-959, 1999.

J. Dijksterhuis et al, "Antibiosis plays a role in the context of direct interaction during antagonism of *Paenibacillus polymyxa* towards *Fusarium oxysporum*," Journal of Applied Microbiology, vol. 86, pp. 13-21, 1999.

* cited by examiner

STRAINS BELONGING TO THE GENUS PAENIBACILLUS AND METHOD OF CONTROLLING PLANT DISEASE BY USING THESE STRAINS OR CULTURE THEREOF

TECHNICAL FIELD

The present invention relates to novel strains belonging to the genus *Paenibacillus* and the control of plant diseases utilizing these strains or cultures thereof. More particularly, the present invention relates to strains belonging to the genus *Paenibacillus* which can exhibit control effect on plant diseases by exhibiting an activity of inducing disease resistance in plants by the production of a substance capable of inducing disease resistance in plants, and more specifically, it relates to novel strains belonging to the genus *Paenibacillus*, such as *Paenibacillus* sp. BS-0048, *Paenibacillus* sp. BS-0074, *Paenibacillus polymyxa* BS-0105, *Paenibacillus* sp. BS-0277, etc.; the control of plant diseases using these strains belonging to the genus *Paenibacillus*; and the control of plant diseases utilizing the novel activity of inducing disease resistance in plant of compounds obtained from cultures of these strains belonging to the genus *Paenibacillus*.

BACKGROUND ART

In the agriculture field, the occurrence of every plant disease causes a marked decrease in the yields of crops and hence the control of the plant diseases is an indispensable means for agricultural techniques. As means for controlling the diseases, there are, for example, the control of the environment for cultivation, the growing of a disease-resistant cultivar, the control of the diseases by the application of agricultural and horticultural fungicides or bactericides, and the biological control of the diseases by the use of organic materials or the like. Of these, the control using agricultural and horticultural fungicides or bactericides is direct and the most effective. However, great dependence on a means comprising direct control of the diseases by the application of a large amount of the fungicides or bactericides is clearly undesirable because of problems such as environmental pollution and influences on environmental living things.

In such a situation, agricultural and horticultural fungicides and bactericides have been developed which are specifically effective against pathogenic fungi and bacteria, respectively, and have a very excellent fungicidal or bactericidal action from the viewpoint of selective toxicity. Such chemicals, however, are disadvantageous in that they tend to bring chemical tolerance to the pathogenic fungi or bacteria. As to a countermeasure against this problem, a plurality of chemicals different in action are applied as a mixture thereof or in rotation.

In order to solve the problem of excessive dependence on such chemical agrochemicals, methods for controlling various crop plant diseases or insect pests by utilizing microorganisms or natural enemies, which are generally present in the natural world, have come to be put to practical use in recent years and a controlling system has come to be improved. For example, patent document 1 has proposed that cells of a microorganism such as *Bacillus subtilis* FR-2, *Bacillus polymyxa* KT-8 or the like should be used as a controller for infection with plant fungi. The efficacy and kind of such a controller are not yet sufficient and a superior biological controller is required.

In order to solve the problem of the appearance of chemical-resistant fungi and bacteria, it is considered the most effective to utilize a substance or a microorganism, which can induce disease resistance in plants.

Although a certain number of substances capable of inducing disease resistance in plant, such as salicylic acid have been known before now, only some of them, such as S-methyl 1,2,3-benzothiazole-7-carboxylate (common name: Acibenzolar-S-methyl) (non-patent document 1 and non-patent document 2) and 3-(2-propyleneoxy)-1,2-benzisothiazole-1,1-dioxide (common name: Probenazole) (non-patent document 3) are actually used as chemicals for controlling plant diseases. Thus, such substances are not satisfactory.

Patent document 2 describes the impartment of resistance to plant diseases by the use of bacteria capable of inducing disease resistance in plants and an organic soil conditioner. This method, however, is not satisfactory.

On the other hand, patent document 3 has reported that an antimicrobially active substance KT-6291A (Fusaricidin A) produced by *Bacillus* sp. KB-291 controls various plant diseases. However, it has been revealed that the antimicrobially active substance KT-6291A described in patent document 3 is inactive not only against cucumber bacterial blight bacterium, a Gram-negative bacterium but also against other Gram-negative bacteria. Patent document 3 does not describe a method for controlling plant diseases caused by Gram-negative bacteria. In addition, it has been revealed that the substance KT-6291A has no antimicrobial activity against *Fusarium* wilt of cucumber fungus, a strain belonging to the genus *Fusarium*. Patent document 3 describes other substances having antimicrobial activity against several microorganisms but does not give any information regarding an activity of inducing disease resistance in plant.

Similarly, non-patent document 4 reveals that an antimicrobially active substance Fusaricidin A is produced by *Bacillus polymyxa* KT-8 but that this substance is inactive against Gram-negative bacteria.

In addition, non-patent document 5 reveals that Fusaricidin B and the like are produced together with Fusaricidin A by *Bacillus polymyxa* KT-8 but that these substances are also inactive against Gram-negative bacteria.

Patent document 1: JP-A-6-253827
Patent document 2: JP-T-2003-529539
Patent document 3: JP-A-2-275898
Non-patent document 1: Plant Physiol. 117, p. 1333-1339 (1998)
Non-patent document 2: Brighton crop protection conference—pest & diseases—1996, 8A-4, CGA2455704
Non-patent document 3: Annu. Rev. Phytopathol. 32, p. 439-59, (1994)
Non-patent document 4: The Journal of Antibiotics VOL. 49, No. 2, p. 129-135 (1996)
Non-patent document 5: The Journal of Antibiotics VOL. 50, No. 3, p. 220-228 (1997)

DISCLOSURE OF THE INVENTION

Problem to be Solved by the Invention

Therefore, a problem for the present invention is to provide a strain belonging to the genus *Paenibacillus* which can exhibit an activity of inducing disease resistance in plant, and moreover, to provide a substance capable of inducing disease resistance in plants.

Another problem for the present invention is to provide a controller for plant diseases and a method for controlling plant diseases, which utilizes the above-mentioned strain or substance.

Means for Solving the Problems

In view of the situation described above, the present inventors earnestly investigated in order to find a superior method for controlling plant diseases, and consequently found that some bacteria, which belong to the genus *Bacillus* when identified by a morphological and physio-characterological test on the strains and belong to the genus *Paenibacillus* when identified by the analysis of the nucleotide sequence of 16S rDNA, have excellent control effect on plant diseases. In addition, it became clear that compounds having an activity of inducing disease resistance in plant are present in cultures of the above-mentioned some bacteria belonging to the genus *Bacillus* or *Paenibacillus*. On the basis of these findings, the present invention has been accomplished.

Thus, the present invention relates to novel strains belonging to the genus *Paenibacillus* which have control effect on plant diseases.

In addition, the present invention relates to strains belonging to the genus *Paenibacillus* which can exhibit control effect on plant diseases by exhibiting an activity of inducing disease resistance in plants by the production of a substance capable of inducing disease resistance in plants.

Further, the present invention relates to a composition containing the above-mentioned strain belonging to the genus *Paenibacillus*.

Still further, the present invention relates to a composition containing one or a combination of two or more of substances capable of inducing disease resistance in plant which are obtained from a culture of the above-mentioned strain belonging to the genus *Paenibacillus*.

Still further, the present invention relates to a controller for plant diseases comprising the above-mentioned composition.

Still further, the present invention relates to a controller for plant diseases containing at least one compound selected from compound 1 (Fusaricidin A), compound 2 (Fusaricidin B), compound 3 and compound 4 which have the following structures:

[Formula 1]

Compound 1

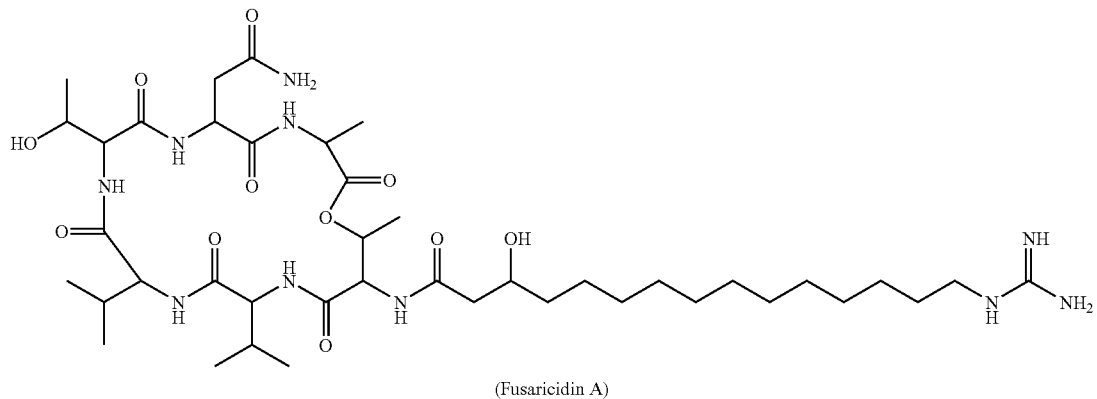

(Fusaricidin A)

[Formula 2]

Compound 2

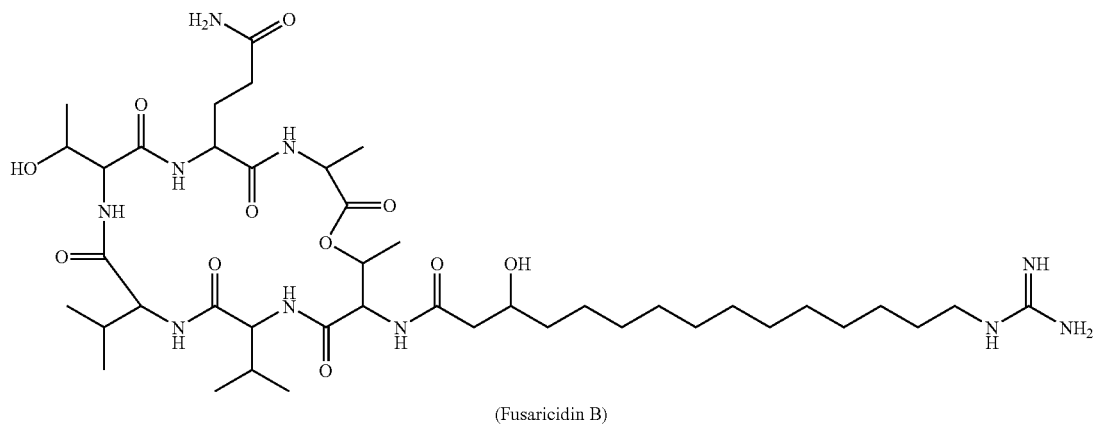

(Fusaricidin B)

[Formula 3]

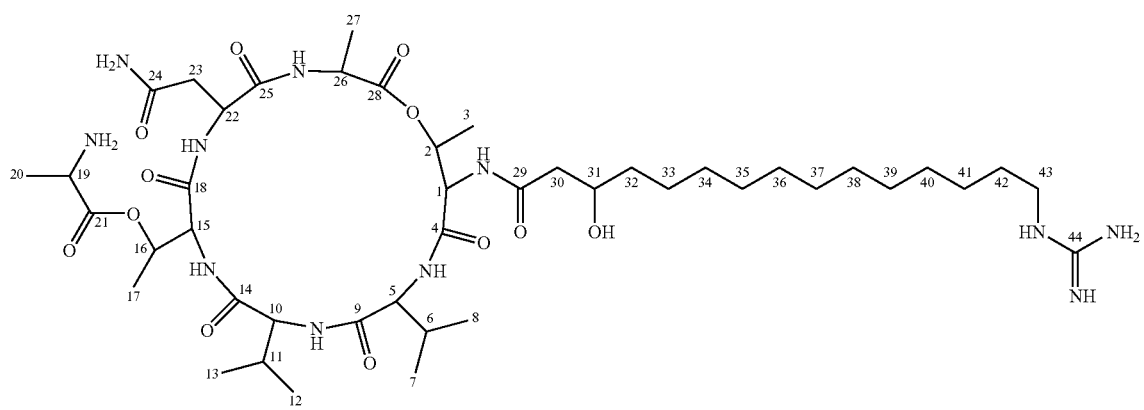

Compound 3

[Formula 4]

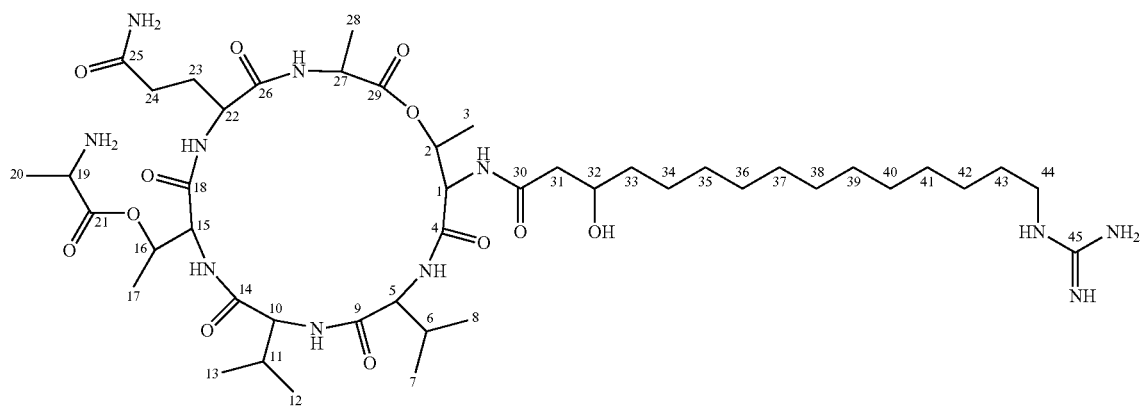

Compound 4

Still further, the present invention relates to a method for controlling plant diseases characterized by protecting plants from infections with plant pathogens by application of the above-mentioned strain belonging to the genus *Paenibacillus*, composition or controller for plant diseases to the plants.

Still further, the present invention relates to novel compounds 3 and 4 having the above structural formulas.

In the present specification, the term "strain belonging to the genus *Paenibacillus*" means a strain that belongs to the genus *Bacillus* when identified by a morphological and physio-characterological test on the strain and belongs to the genus *Paenibacillus* when identified by the analysis of the base sequence of 16S rDNA.

ADVANTAGES OF THE INVENTION

The strains belonging to the genus *Paenibacillus* of the present invention can control plant diseases caused by Gram-negative bacteria (e.g. strains belonging to the genus *Pseudomonas*) and strains belonging to the genus *Fusarium* by exhibiting an activity of inducing disease resistance in plants.

In addition, the novel microorganisms found by the present invention, i.e., *Paenibacillus* sp. BS-0048, *Paenibacillus* sp. BS-0074, *Paenibacillus polymyxa* BS-0105 and *Paenibacillus* sp. BS-0277 can control the plant diseases caused by the Gram-negative bacteria and the strains belonging to the genus *Fusarium* and moreover, can control plant diseases caused by common plant pathogenic fungi, for example, various pathogenic fungi such as strains belonging to the genus *Colletotrichum* and strains belonging to the genus *Glomerella*. Here, for example, the term "*Paenibacillus* sp. BS-0048" means one and the same strain which may be named *Bacillus* sp. BS-0048 when identified by a morphological and physio-characterological test on the strain and may be named *Paenibacillus* sp. BS-0048 when identified by the analysis of the base sequence of 16S rDNA. The term "*Paenibacillus polymyxa* BS-0105" means one and the same strain which may be named *Bacillus* sp. BS-0105 belonging to the genus *Bacillus*, when identified by a morphological and physio-characterological test on the strain and may be named *Paenibacillus polymyxa* BS-0105 belonging to the species *polymyxa* of the genus *Paenibacillus*, when identified by the analysis of the base sequence of 16S rDNA.

Furthermore, compound 1 (Fusaricidin A), compound 2 (Fusaricidin B), compound 3 and compound 4, which are produced by strains belonging to the genus *Paenibacillus*, have an activity of inducing disease resistance in plant and hence have an ability to protect plants from infections with plant pathogens, so that they are effective in controlling the plant diseases.

BEST MODE FOR CARRYING OUT THE INVENTION

Figure 1:
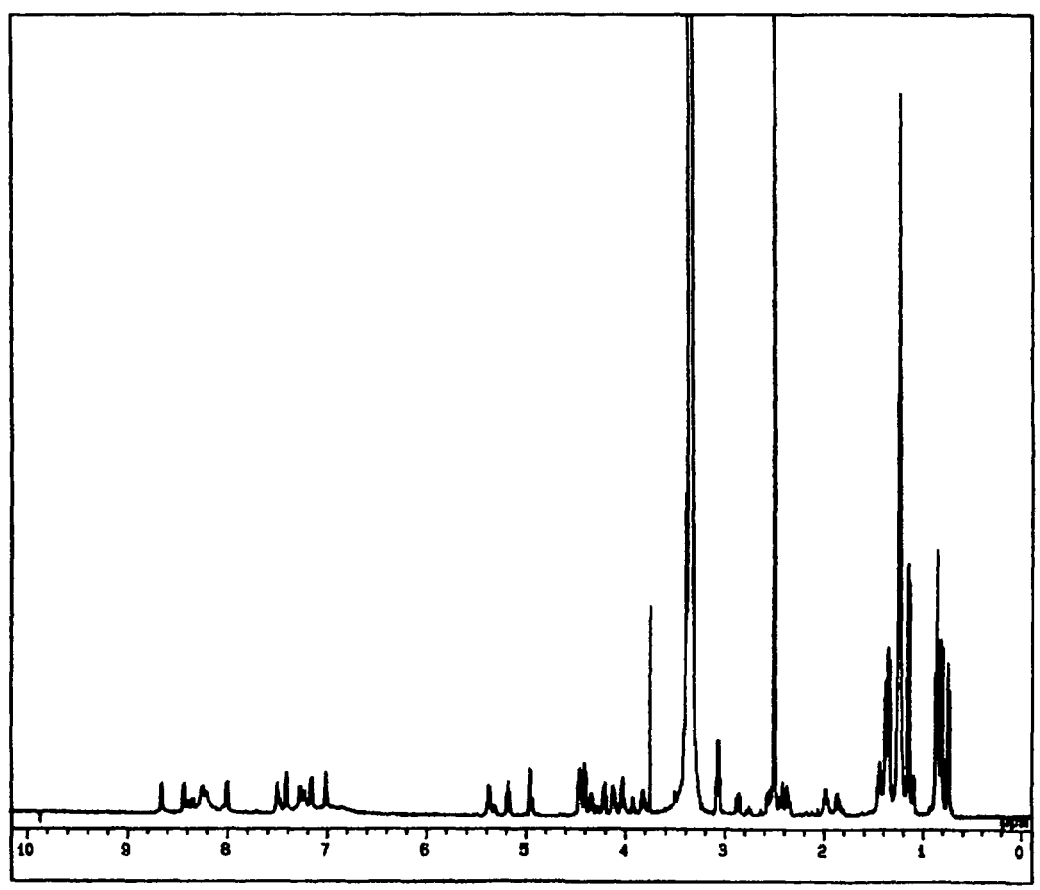
FIG. 1 A proton nuclear magnetic resonance spectrum (DMSO-d6) of the novel compound 3 of the present invention.

By the present invention, there are provided novel strains of the genus *Paenibacillus* having control effect on plant diseases, and there are provided strains of the genus *Paenibacillus* which can exhibit control effect on plant diseases by exhibiting an activity of inducing disease resistance in plants by the production of a substance capable of inducing disease resistance in plants. As the substance capable of inducing disease resistance in plants according to the present invention, the above-mentioned compound 1 (Fusaricidin A), compound 2 (Fusaricidin B), compound 3 and compound 4 are exemplified.

The term "activity of inducing disease resistance in plant" used here means an activity of imparting so-called "induced disease resistance" against the plant. Strains belonging to the genus *Paenibacillus* and capable of producing a substance having such an activity, and substances capable of inducing resistance to plant diseases, such as compound 1 (Fusaricidin A), compound 2 (Fusaricidin B), compound 3 and compound 4, can protect plants from infections with plant pathogens. Therefore, they protect the plants from infections with the plant pathogens by exhibiting the activity of inducing disease resistance in plant without exhibition of direct antimicrobial activity, so that they can control the plant diseases.

Specific examples of such strains belonging to the genus *Paenibacillus* are the novel strains *Paenibacillus* sp. BS-0048, *Paenibacillus* sp. BS-0074, *Paenibacillus polymyxa* BS-0105 and *Paenibacillus* sp. BS-0277 found by the present invention and their variants. As the variant, any variant may be used so long as it is induced, for example, by spontaneous mutation, a physical cause (e.g. ultraviolet rays) or a chemical mutagen (e.g. a base compound), and can exhibit control effect on plant diseases by exhibiting the function aimed at by the present invention, i.e., an activity of inducing disease resistance in plants by the production of a substance capable of inducing disease resistance in plants, for example, at least one compound selected from compound 1 (Fusaricidin A), compound 2 (Fusaricidin B), compound 3 and compound 4.

As the strains of the genus *Paenibacillus* used in the present invention, there may be used even strains which can be said to belong to the genus *Bacillus* when identified by a morphological and physio-characterological test on the strains, so long as they belong to the genus *Paenibacillus* when identified by the analysis of the base sequence of 16S rDNA.

The strains belonging to the genus *Paenibacillus* of the present invention can control plant diseases caused by Gram-negative bacteria and strains belonging to the genus *Fusarium*, by exhibiting an activity of inducing disease resistance in plants by the production of a substance capable of inducing disease resistance in plants. In addition, such a substance capable of inducing disease resistance in plants, such as the above-mentioned compound 1 (Fusaricidin A), compound 2 (Fusaricidin B), compound 3 and compound 4 can also control in themselves the plant diseases caused by Gram-negative bacteria and strains belonging to the genus *Fusarium*, by exhibiting the activity of inducing disease resistance in plants.

As the plant diseases caused by Gram-negative bacteria, plant diseases caused by strains belonging to the genus *Pseudomonas* are exemplified. Specific examples of the plant diseases are bacterial blight of plants of the Cucurbitaceae, such as bacterial blight (*Pseudomonas syringae* pv. *lachrymans*) of melon and cucumber, and sheath brown rot (*Pseudomonas fuscovaginae*) of rice. As the plant diseases caused by strains belonging to the genus *Fusarium*, there are exemplified scab (*Fusarium graminearum, Fusarium avenaceum, Fusarium culmorum*) of barley, wheat, oats and rye, *Fusarium* wilt (*Fusarium oxysporum* f. sp. *cucumerium*) of cucumber, *Fusarium* wilt (*Fusarium oxysporum* f. sp. *melonis*) of melon, and *Fusarium* wilt (*Fusarium oxysporum* f. sp. *lycopersici*) of tomato.

The strains belonging to the genus *Paenibacillus* of the present invention, such as novel strains *Paenibacillus* sp. BS-0048, *Paenibacillus* sp. BS-0074, *Paenibacillus polymyxa* BS-0105 and *Paenibacillus* sp. BS-0277 can control the above-exemplified plant diseases caused by Gram-negative bacteria and strains belonging to the genus *Fusarium*, and moreover, they can control plant diseases caused by common plant pathogenic fungi, for example, various pathogenic fungi such as strains belonging to the genus *Colletotrichum* and strains belonging to the genus *Glomerella*. The plant diseases caused by the strains belonging to the genus *Colletotrichum* include, for example, anthracnose of plants of the Cucurbitaceae, such as anthracnose (*Colletotrichum orbiculare*) of cucumber, and anthracnose (*Colletotrichum acutatum*) of strawberry. The plant diseases caused by the strains belonging to the genus *Glomerella* include, for example, ripe rot (*Glomerella cingulata*) of grape and anthracnose (*Glomerella cingulata*) of strawberry.

The strains belonging to the genus *Paenibacillus* of the present invention are effective also against plant diseases other than the above-exemplified plant diseases, such as gray mold (*Botrytis cinerea*) and stem rot (*Sclerotinia sclerotiorum*) of various crop plants; blast (*Pyricularia oryzae*), sheath blight (*Thanatephorus cucumeris*) and Helminthosporium leaf spot (*Cochliobolus miyabeanus*) of rice; scab (*Venturia inaequalis*), *Alternaria* leaf spot (*Alternaria mali*) and canker (*Valsa ceratosperma*) of apple; black spot (*Alternaria kikuchiana*) and scab (*Venturia nashicola*) of pear; melanose (*Diaporthe citri*), bluemold (*Penicillium italicum*) and canker (*Xanthomonas campestris* pv. *citri*) of citrus; *Phomopsis* rot (*Phomopsis* sp.) and brown rot (*Monilinia fructicola*) of peach; anthracnose (*Gloeosporium kaki*) and angular leaf spot (*Cercospora kaki*) of Japanese persimmon; powdery mildew (*Erysiphe graminis*), rust (*Puccinia graminis, P. striformis, P. recondita*), loose smut (*Ustilago nuda*) and scab (*Gibberella zeae, Monographella nivalis*) of barley, wheat, oats and rye; powdery mildew (*Sphaerotheca cucurbitae*), gummy stem blight (*Didymella bryoniae*) and downy mildew (*Pseudoperonospora cubensis*) of cucumber; leaf mold (*Fulvia fulva*) of tomato; *Verticillium* wilt (*Verticillium dahliae*), brown rot (*Phytophthora capsici*) and bacterial wilt (*Ralstonia solanacearum*) of eggplant; brown spot (*Alternaria alternata*) of tobacco; leaf spot (*Cercospora beticola*) of beet; late blight (*Phytophthora infestans*) of potato; purple stain (*Cercospora kikuchii*) of soybean; downy mildew (*Pernospora brassicae*) of Japanese radish; downy mildew (*Peronospora spinaciae*) of spinach; bacterial blight (*Xanthomonas campestris* pv. *vitians*) and bacterial soft rot (*Erwinia carotovora* subsp. *carotovora*) of lettuce; black rot (*Xanthomonas campestris* pv. *campestris*) of cabbage; club root (*Plasmodiophora brassicae*) of vegetables of Cruciferae; seedling blight (*Pyythium* sp) of various crop plants; violet root rot (*Helicobasidium mompa*) of fruit trees; large patch (*Rhizoctonia solani*) and *Curvularia* leaf blight (*Curvularia* sp.) of lawn grass; etc.

In addition, the strains belonging to the genus *Paenibacillus* of the present invention and the substances capable of inducing disease resistance in plant according to the present invention, such as the above-mentioned compound 1 (Fusaricidin A), compound 2 (Fusaricidin B), compound 3 and compound 4 exhibit in themselves an activity of inducing disease resistance in plant and hence protect plants from infections with plant pathogens, so that they can control the plant diseases. As the plant pathogens, not only the above-exemplified various bacteria and fungi but also viruses may be exemplified.

As the fungi, there are exemplified fungi capable of causing the following plant diseases: gray mold (*Botrytis cinerea*) and stem rot (*Sclerotinia sclerotiorum*) of various crop plants; blast (*Pyricularia oryzae*), sheath blight (*Thanatephorus cucumeris*) and *Helminthosporium* leaf spot (*Cochliobolus miyabeanus*) of rice; scab (*Venturia inaequalis*), *Alternaria* leaf spot (*Alternaria mali*) and canker (*Valsa ceratosperma*) of apple; black spot (*Alternaria kikuchiana*) and scab (*Venturia nashicola*) of pear; melanose (*Diaporthe citri*) and blue mold (*Penicillium italicum*) of citrus; *Phomopsis* rot (*Phomopsis* sp.) and brown rot (*Monilinia fructicola*) of peach; anthracnose (*Gloeosporium kaki*) and angular leaf spot (*Cercosporakaki*) of Japanese persimmon; ripe rot (*Glomerella cingulata*) of grape; powdery mildew (*Erysiphe graminis*), rust (*Puccinia graminis, P. striformis, P. recondita*), loose smut (*Ustilago nuda*) and scab (*Monographella nivalis*) of barley, wheat, oats and rye; powdery mildew (*Sphaerotheca cucurbitae*), gummy stem blight (*Didymella bryoniae*) anthracnose (*Colletotrichum orbiculare*) and downy mildew (*Pseudoperonospora cubensis*) of cucumber; leaf mold (*Fulvia fulva*) of tomato; *Verticillium* wilt (*Verticillium dahliae*) and brown rot (*Phytophthora capsici*) of eggplant; anthracnose (*Collectorichum acutatum, Glomerella cingulata*) of strawberry; brown spot (*Alternaria alternata*) of tobacco; leaf spot (*Cercospora beticola*) of beet; late blight (*Phytophthora infestans*) of potato; purple stain (*Cercospora kikuchii*) of soybean; downy mildew (*Pernospora brassicae*) of Japanese radish; downy mildew (*Peronospora spinaciae*) of spinach; club root (*Plasmodiophora brassicae*) of vegetables of Cruciferae; seedling blight (*Pythium* sp) of various crop plants; violet root rot (*Helicobasidium mompa*) of fruit trees; large patch (*Rhizoctonia solani*) and *Curvularia* leaf blight (*Curvularia* sp.) of lawn grass; etc.

Besides the above-exemplified fungi, as the bacteria, there are exemplified bacteria capable of causing the following plant diseases: canker (*Xanthomonas campestris* pv. *citri*) of citrus; bacterial wilt (*Ralstonia solanacearum*) of eggplant; bacterial blight (*Xanthomonas campestris* pv. *vitians*) and bacterial soft rot (*Erwinia carotovora* subsp. *carotovora*) of lettuce; and black rot (*Xanthomonas campestris* pv. *campestris*) of cabbage.

As the viruses, there are exemplified viruses capable of causing the following plant diseases: cucumber mosaics (cucumber mosaic cucumovirus, watermelon mosaic2 potyvirus, zucchini yellow mosaic poryvirus), tomato viral diseases (tobacco necrosis necrovirus), strawberry viral diseases (strawberry crincle cytorhabdovirus, strawberry latent C virus, soybean dwarf luteovirus, strawberry mottle virus, strawberry pseudo mild-yellow edge carlavirus, strawberry vein banding caulimovirus, tobacco mosaics tobamovirus, tobacco necrosis necrovirus), cabbage mosaic (cauliflower mosaic caulimovirus, cucumber mosaic cucumovirus, turnip mosaic poryvirus), soybean viral diseases (southern bean mosaic sobemovirus, peanut stunt cucumovirus, bean common mosaic poryvirus, broad bean wilt fabavirus) and potate leaf-roll (potate leafroll luteovirus).

When the strain of the genus *Paenibacillus* of the present invention is used for controlling plant diseases, spores, vegetative cells, whole culture or the like of the strain of the genus *Paenibacillus* may be usually used. They may be prepared from a culture obtained by cultivating the strain of the genus *Paenibacillus* by a conventional method. The whole culture obtained may be prepared into whole culture powder, for example, by freeze-drying the whole culture as it is. The vegetative cells may be prepared as a cell precipitate, for example, by centrifuging whole culture after the cultivation to remove contaminants, further centrifuging the resulting supernatant, and then washing the cells precipitated. In addition, the spores may be prepared as freeze-dried spore powder, for example, by suspending the cell precipitate obtained above in distilled water and freeze-drying the resulting suspension.

Although the strain of the genus *Paenibacillus* used in the present invention is usually viable cells, it may be cells killed by heat treatment or the like. The viable cells referred to here include, as described above, viable cells obtained from the culture, dried cells obtained from the viable cells, cells separated from the culture by a conventional method such as filtration, centrifugation or the like, and cells dried after separation and collection.

The strains belonging to the genus *Paenibacillus*, such as *Paenibacillus* sp. BS-0048, *Paenibacillus* sp. BS-0074, *Paenibacillus polymyxa* BS-0105, *Paenibacillus* sp. BS-0277, etc. are cultured by a conventional cultivation method for common bacteria. They may be cultured every imaginable method such as solid culture or liquid culture (e.g. test tube shaking culture, reciprocal shaking culture, rotary shaking culture, jar fermentor culture or tank culture). As a culture medium, a proper combination of various carbon sources, nitrogen sources, organic salts and inorganic salts may be used. In general, the carbon sources include, for example, glucose, starch, glycerol, dextrin, sucrose, and animal and vegetable oils. The organic nitrogen sources include, for example, yeast extract, soybean flour, corn steep liquor, wheat germ, meat extract and peptone. The inorganic nitrogen sources include, for example, sodium nitrate, ammonium nitrate, ammonium sulfate and ammonium acetate. The organic salts and inorganic salts include, for example, acetates such as sodium acetate, etc.; carbonates such as calcium carbonate, sodium carbonate, etc.; chlorides such as sodium chloride, potassium chloride, etc.; phosphates such as potassium dihydrogenphosphate, disodium hydrogenphosphate, etc.; and sulfates such as ferrous sulfate, zinc sulfate, copper sulfate, etc. Although the cultivation temperature may be properly varied so long as the microorganism can be grown, it is preferably in the range of 20° C. to 40° C. Usually, the cultivation is carried out under aerobic conditions. Particularly when carried out in a jar fermentor or a culture tank, the cultivation is carried out while introducing sterile air. A method and conditions for the cultivation are not particularly limited so long as the microorganism can be grown.

Compound 1 (Fusaricidin A) and compound 2 (Fusaricidin B), which are used in the present invention as a substance capable of inducing disease resistance in plant, may be obtained from a culture of the novel strain of the genus *Paenibacillus* (e.g. *Paenibacillus* sp. BS-0048, *Paenibacillus* sp. BS-0074, *Paenibacillus polymyxa* BS-0105 or *Paenibacillus* sp. BS-0277) found by the present invention, or a strain of the genus *Bacillus*, such as *Bacillus* sp. KB-291 (JP-A-2-275898) or *Bacillus polymyxa* KT-8 (The Journal of Antibiotics VOL. 49, No. 2, p. 129-135 (1996); The Journal of Antibiotics VOL. 50, No. 3, p. 220-228 (1997)) which are known to produce the above-mentioned compounds. Compound 3 and compound 4 may be obtained from a culture of the above-mentioned novel strain of the genus *Paenibacillus* found by the present invention. Specifically, such a strain is cultured by a conventional method and the above-mentioned compound may be obtained from the resulting culture broth by the method described in the above-mentioned references or a combination of conventional purification methods. The above-mentioned compound may be obtained, for example, by extracting the culture broth with butanol, ethyl acetate or the like and subjecting the extract solution to high performance liquid chromatography.

The strains of the genus *Paenibacillus* or the substances capable of inducing resistance to plant diseases, such as compound 1 (Fusaricidin A), compound 2 (Fusaricidin B), compound 3 and compound 4, which are used for controlling the plant diseases in the present invention, may be used as they are without adding any other component. If necessary, there may be used a composition prepared by mixing the above-mentioned strain or substance with any of various carriers such as solid carriers or liquid carriers, or a formulation obtained by preparing the strain or substance into a wettable powder, a soluble concentrate, a suspension, granules, a dust, microcapsules, a paste or the like by the addition of adjuvants for formulation, such as additives.

Such a formulation contains the strain of the genus *Paenibacillus* of the present invention usually in an amount of approximately 0.1% to 99% by weight (the weight of the bacterium is wet weight). The formulation preferably contains the strain of the genus *Paenibacillus* of the present invention in an amount of about $10^3$ to about $10^{11}$ colony-forming units (hereinafter abbreviated as CFU) per g of the formulation. When spores, vegetative cells or whole culture of the strain of the genus *Paenibacillus* is used, the formulation preferably contains the spores, vegetative cells or whole culture in an amount of approximately $10^3$ to $10^{11}$ CFU per g of the formulation, or in an amount of usually approximately 0.1% to 99% by weight (wet weight). In the case of the substances capable of inducing disease resistance in plant, the formulation preferably contains at least one compound selected from compound 1 (Fusaricidin A), compound 2 (Fusaricidin B), compound 3 and compound 4 in an amount of 0.01% to 99%.

The solid carriers used in the formulation include, for example, mineral powders (e.g. kaoline clay, bentonite, diatomaceous earth, synthetic hydrated silicon oxide, talc, quartz, vermiculite and perlite), inorganic salts (e.g. ammonium sulfate, ammonium phosphate, ammonium nitrate, urea and ammonium chloride), organic powders (wheat flour, soybean flour, wheat bran, chitin, rice bran, skim milk powder and whole milk powder), activated carbon and calcium carbonate. The liquid carriers include, for example, water, glycerol, vegetable oils (e.g. soybean oil and rapeseed oil), liquid animal oils (e.g. fish oil), ethylene glycol, poly(ethylene glycol)s, propylene glycol and poly(propylene glycol)s.

The adjuvants for formulation include, for example, anti-freezing agents such as casein, gelatin, polysaccharides (e.g. starch powder, gum arabic, cellulose derivatives and alginic acid), lignin derivatives, bentonite, sugars, vegetable oils, mineral oils, synthetic water-soluble polymers (e.g. poly(vinyl alcohol)s, poly(acrylic acid)s), propylene glycol, ethylene glycol, etc.; defoaming agents such as silicone type compounds; and thickening agents such as natural polysaccharides (e.g. Xanthan gum), inorganic substances (e.g. aluminum and bentonite), synthetic water-soluble polymers (e.g. poly(acrylic acid)s).

The formulation may be used in admixture with insecticides, nematicides, acaricides, fungicides, bactericides, herbicides, plant growth regulators, spreaders, fertilizers, microbial materials, soil amendments and the like, or may be used together with them without mixing therewith.

In the control of plant diseases according to the present invention, the applying dosage (wet dosage) of the active ingredient of the strain of the genus *Paenibacillus* used is usually about 0.1 g to about 10000 g, preferably about 10 g to about 1000 g, per 10 ares. When the wettable powder, suspension, microcapsules or the like is used after being diluted with water, the cell concentration at the time of application is usually about $10^3$ CFU/mL to about $10^{11}$ CFU/mL, preferably about $10^5$ CFU/mL to about $10^9$ CFU/mL. The granules, dust, paste and the like may be applied as they are in the form of such a formulation without dilution.

When spores, vegetative cells or whole culture of the strain of the genus *Paenibacillus* is used, the applying dosage thereof is preferably about 0.1 g to about 10000 g (wet weight) per 10 ares. When the spores or vegetative cells are used after being diluted with water, the concentration thereof at the time of application is preferably about $10^3$ to about $10^{10}$ CFU/mL. The applying dosage of the substance capable of inducing disease resistance in plant is preferably approximately 0.001 g to 10000 g per 10 ares. When at least one compound selected from compound 1 (Fusaricidin A), compound 2 (Fusaricidin B), compound 3 and compound 4 is used after being diluted with water, the concentration thereof at the time of application is preferably 0.1 to 1000 μg/mL.

In the control of plant diseases according to the present invention, the strain of the genus *Paenibacillus* or substance capable of inducing disease resistance in plants of the present invention is preferably applied to the stalks and leaves, rooting zone and/or seeds of a plant. For actually applying the strain or substance, there are, for example, conventional methods such as a method of applying granules to a plant foot or soil and a method of applying a diluted liquid or an undiluted liquid to a plant foot or soil. Besides these methods, there may be adopted, for example, the same spraying method as a method for controlling diseases in above-ground part; a method of coating plant seeds with, or immersing them in, a mixture or each of the strain of the genus *Paenibacillus* or substance capable of inducing disease resistance in plants of the present invention, a solid carrier, an adhesive agent called a binder, and the like; a method of applying the strain or substance in admixture with a fertilizer, a soil amendment, compost and the like or applying the strain or substance together with them without mixing therewith; and a method using a microbial material obtained by adsorbing the strain of the genus *Paenibacillus* or substance capable of inducing disease resistance in plants of the present invention on a solid carrier and or without adding thereto organic nutrients (e.g. rice bran, malt extract and amino acids), fertilizer components, etc.

Both applying dosage and applying concentration of such formulations are varied depending on conditions such as the kind of the formulation, an application time, an application site, an application method, a cultivation method, the kind of a crop plant, the kind of a plant disease, the degree of damage, etc., and may be increased or decreased irrespective of the above-mentioned ranges.

The control of plant diseases according to the present invention is explained below in further detail with examples of the separation of bacteria, production examples, formulation examples, test examples, cultivation examples, extraction examples, purification examples, preparation examples and evaluation examples, but the present invention is not limited by these working examples.

Bacteria Separation Example 1

Separation and Identification of Novel Strains *Paenibacillus* sp. BS-0048, *Paenibacillus* sp. BS-0074, *Paenibacillus polymyxa* BS-0105 and *Paenibacillus* sp. BS-0277

(1) Separation of the Strains

The rooting zone soils and roots of tomato, eggplant, green pepper, cucumber, melon, spinach, strawberry, Japanese radish, Chinese yam and the like were collected from cultivation fields in various places of the whole of Japan. In a lidded glass bottle containing 90 mL of sterilized water was placed 10 g of the rooting zone soil or the root, and subjected to ultrasonication or shaking treatment. The resulting suspension was properly diluted and 1 mL of the dilution was mixed and diluted with albumin agar medium (egg albumin 0.25 g, D-glucose 1 g, dipotassium phosphate 0.5 g, magnesium sulfate 0.2 g, iron (III) sulfate trace, distilled water 1 L, pH 6.8 to 7.0), followed by cultivation at 30° C. for 5 to 10 days. The thus formed colonies were separated.

(2) Identification of the Strains by a Morphological and Physio-Characterological Test The strains exemplified herein are microorganisms separated from tomato cultivation soil, Chinese yam cultivation soil and organic successive application soil and were named BS-0048 strain, BS-0074 strain, BS-0105 strain and BS-0277 strain as strain codes. The following Table 1 shows the results of a morphological and physio-characterological test on BS-0048 strain, BS-0074 strain, BS-0105 strain and BS-0277 strain.

TABLE 1

Table 1: Results of a morphological and physio-characterological test on BS-0048 strain, BS-0074 strain, BS-0105 strain and BS-0277 strain

| Properties | BS-0048 strain | BS-0074 strain | DS-0105 strain | BS-0277 strain |
| --- | --- | --- | --- | --- |
| Shape: | Rod | Rod | Rod | Rod |
| Dimensions (μm) | 0.8-1.5 | 0.8-1.2 | 0.8-1.5 | 0.8-1.5 |
| Width (μm) | 4-8 | 2-8 | 2-8 | 4-8 |
| Gram reactivity | V | V | V | V |
| Shape and position of spare: | | | | |
| Oval | + | + | + | + |
| Spherical | + | + | + | + |
| Center | + | + | + | + |
| End | + | + | + | + |
| Motile | + | + | + | ± |
| Anaerobic growth | + | − | + | + |
| V-P reaction | − | − | − | − |
| Growth temperature: | | | | |
| Maximum (° C.) | 10 | 15 | 10 | 10 |
| Minimum (° C.) | 45 | 50 | 45 | 45 |
| Growth range: | | | | |
| Medium pH5.7 | + | + | + | + |
| Nutrient broth | + | + | + | + |
| NaCl (5%) | + | + | − | − |
| NaCl (7%) | − | − | − | − |
| NaCl (10%) | − | − | − | − |
| Production of acid from sugar: | | | | |
| Glucose | + | + | + | + |
| Trehalose | + | + | + | + |
| Xylose | + | + | + | + |
| Arabinose | + | + | + | + |
| Mannitol | + | + | + | + |
| Casein utilization | + | + | + | + |

Although BS-0048 strain and BS-0277 strain had the highest similarity to *B. polymyxa*, each of them was judged as a novel strain because they were different from *B. polymyxa* in V-P reactivity. Although BS-0105 strain was similar to *B. polymyxa* or *B. macerans*, it was different from these strains in V-P reactivity and casein utilization. The result of identification with a BiOLOG identification apparatus indicated that BS-0105 strain corresponded to *B. macerans* and *B. polymyxa*, but BS-0105 strain was judged as a novel strain because it was a different strain having a low similarity to *B. macerans* and *B. polymyxa*. Although BS-0074 strain had a slightly higher similarity to *B. halodurans*, it was judged as a novel strain because there were several differences between BS-0074 strain and *B. halodurans* with regard to utilization.

As a result of the above-mentioned morphological and physio-characterological test, all of BS-0048 strain, BS-0074 strain, BS-0105 strain and BS-0277 strain separated from the tomato cultivation soil, Chinese yam cultivation soil or organic successive application cultivation soil were identified as *Bacillus* sp. and deposited as follows in Patented Organism Deposition Center (IPOD), Industrial Technology General Research Institute (Independent Administrative Corporation): BS-0048 strain was deposited as *Bacillus* sp. BS-0048 (receipt date: Jun. 18, 2004; receipt number: FERM P-20085), BS-0074 strain was deposited as *Bacillus* sp. BS-0074 (receipt date: Jun. 18, 2004; receipt number: FERM P-20086), BS-0105 strain was deposited as *Bacillus* sp. BS-0105 (receipt date: Jun. 18, 2004; receipt number: FERM P-20087), and BS-0277 strain was deposited as *Bacillus* sp. BS-0277 (receipt date: Jun. 18, 2004; receipt number: FERM P-20088).

(3) Identification by 16S rDNA Base Sequence Analysis

The base sequence (about 1500 bp) of 16S rDNA (16S rRNA gene) of *Bacillus* sp. BS-0105 strain was determined and the homology of the base sequence determined was looked up in the bacterial type strain data base and GenBank/DDBJ/EMBL. As a result, the 16S rDNA base sequence of *Bacillus* sp. BS-0105 strain had the highest homology with 16S rDNA of *Paenibacillus polymyxa* at a homology percentage of 98.7%. Molecular phylogeny analysis was carried out by preparing a molecular phylogenic tree and as a result, it was considered that BS-0105 strain is very likely to be nearly related to *P. polymyxa*. In addition, BS-0105 strain and a type strain of *P. polymyxa* were compared with respect to DNA-DNA homology values by employing hybridization, to find that BS-0105 strain had a percentage of homology with the type strain of 70% or more.

On the basis of the above facts, *Bacillus* sp. BS-0105 strain was identified as *Paenibacillus polymyxa* though only a low homology was shown as a result of identification with a BioLOG identification apparatus. Therefore, *Bacillus* sp. BS-0105 strain was named *Paenibacillus polymyxa* BS-0105.

The partial base sequence (about 500 bp) of 16S rDNA (16S rRNA gene) of each of *Bacillus* sp. BS-0048 strain, BS-0074 strain and BS-0277 strain was determined and the homology of the base sequence determined was looked up in the bacterial type strain data base and GenBank/DDBJ/EMBL. As a result, the 16S rDNA base sequence of each of *Bacillus* sp. BS-0048 strain and BS-0277 strain had the highest homology with 16S rDNA of *Paenibacillus polymyxa* at homology percentages of 98.5% and 97.5%, respectively. The 16S rDNA base sequence of *Bacillus* sp. BS-0074 strain had the highest homology with 16S rDNA of *Paenibacillus eligii* at a homology percentage of 98.4%. Whichever database was used for picking up the homology, 16S rDNAs of 30 higher-ranking strains having a higher homology with each of *Bacillus* sp. BS-0048 strain, BS-0074 strain and BS-0277 strain were those derived from *Paenibacillus*. Molecular phylogeny analysis was carried out by preparing a molecular phylogenic tree to find that *Bacillus* sp. BS-0048 strain and BS-0277 strain were included in a cluster including *P. polymyxa* as the central figure and that *Bacillus* sp. BS-0048 strain showed the same phylogenetic branch as that of *P. elgii*.

On the basis of the above facts, *Bacillus* sp. BS-0048 strain, *Bacillus* sp. BS-0074 strain and *Bacillus* sp. BS-0277 strain were identified as strains of the genus *Paenibacillus*. Therefore, they were named *Paenibacillus* sp. BS-0048, *Paenibacillus* sp. BS-0074 and *Paenibacillus* sp. BS-0277, respectively.

According to the above new naming, the names of the strains deposited in Patented Organism Deposition Center (IPOD), IPOD (Independent Administrative Corporation) Industrial Technology General Research Institute, Chuo-dairoku, Higashi 1-1-1, Tsukuba City, Ibaraki Prefecture, Japan 305-8566 were changed to the new names, and the internal deposition of these strains was changed to international deposition based on Budapest Treaty. As a result, BS-0048 strain, BS-0074 strain, BS-0105 strain and BS-0277 strain were deposited as follows in Patented Organism Deposition Center (IPOD), IPOD (Independent Administrative Corporation) Industrial Technology General Research Institute, Chuo-dairoku, Higashi 1-1-1, Tsukuba City, Ibaraki Prefecture, Japan 305-8566: BS-0048 strain was deposited as *Paenibacillus* sp. BS-0048 (control transfer date: Jul. 22, 2005 (22.07.2005); receipt number: IPOD FERM BP-10377), BS-0074 strain was deposited as *Paenibacillus* sp. BS-0074 (control transfer date: Jul. 22, 2005 (22.07.2005); receipt number: IPOD FERM BP-10378), BS-0105 strain was deposited as *Paenibacillus polymyxa* BS-0105 (control transfer date: Jul. 22, 2005 (22.07.2005); receipt number: IPOD FERM BP-10379), and BS-0277 strain was deposited as *Paenibacillus* sp. BS-0277 (control transfer date: Jul. 22, 2005 (22.07.2005); receipt number: IPOD FERM BP-10380).

Production Example 1

Cultivation of *Paenibacillus* sp. BS-0048, *Paenibacillus* sp. BS-0074, *Paenibacillus polymyxa* BS-0105 and *Paenibacillus* sp. BS-0277

A loopful of stored cells of each of strains BS-0048, BS-0074, BS-0105 and BS-0277 of the present invention were inoculated into a 50-mL test tube containing 10 mL of YPMG medium (D-glucose 10 g, meat extract 1 g, yeast extract 3 g, peptone 5 g, distilled water 1 L, pH7.0) and then cultured for 3 days in the dark at 25° C. and a number of shakes of 100 shakes/min. A 100-mL Erlenmeyer flask containing 10 mL of a medium (D-glucose 20 g, soluble starch 10 g, peptone 10 g, yeast extract 10 g, malt extract 10 g, soybean flour 15 g, distilled water 1 L) was inoculated with 0.1 mL of the culture of each of strains BS-0048, BS-0105 and BS-0277 obtained by the pre-cultivation described above. On the other hand, a 100-mL Erlenmeyer flask containing 10 ml of YPMG medium was inoculated with 0.1 mL of the culture of strain BS-0074. Then, all of the above-mentioned cultures were incubated for 4 days under conditions of a number of revolutions of 200 rpm and 25° C.

Production Process 2

Cultivation of *Paenibacillus polymyxa* BS-0105

A loopful of stored cells of strain BS-0105 of the present invention were inoculated into a 250-mL Erlenmeyer flask containing 100 mL of YPMG medium, and then cultured for 7 days in the dark at 30° C. and a number of shakes of 100 shakes/min.

Production Example 3

Preparation of Whole Culture of *Paenibacillus polymyxa* BS-0105

About 1 L of whole culture of strain BS-0105 obtained according to Production Example 1 was centrifuged at 1500 rpm for 5 minutes to remove contaminants derived from the medium, and then the supernatant was centrifuged at 8000 rpm for 20 minutes to precipitate cells. The precipitate was washed with 0.8% physiological saline and re-centrifuged at 8000 rpm for 20 minutes. The above procedure was repeated twice to obtain a cell precipitate.

Production Example 4

Preparation of Freeze-Dried Cell (Spore) Powder of *Paenibacillus polymyxa* BS-0105

A washed cell precipitate obtained from 300 mL of the same culture as described above in Production Example 3 was suspended in 50 mL of distilled water and the resulting suspension was charged into a freeze-drying machine to obtain 2.13 g of freeze-dried cell (spore) powder containing cells in an amount of $8.8\times10^9$ CFU/g.

Production Example 5

Preparation of Freeze-Dried Cell (spore) Powder of *Paenibacillus polymyxa* BS-0105

A washed cell precipitate obtained from 300 mL of the same culture as described above in Production Example 3 was suspended in 50 mL of 20% skim milk and the resulting suspension was charged into a freeze-drying machine to obtain 11.08 g of freeze-dried cell (spore) powder containing cells in an amount of $3.5\times10^9$ CFU/g.

Production Example 6

Preparation of Freeze-Dried Cell (spore) Powder of *Paenibacillus polymyxa* BS-0105

A washed cell precipitate obtained from 300 mL of the same culture as described above in Production Example 3 was suspended in 50 mL of a 5% ammonium sulfate solution and the resulting suspension was charged into a freeze-drying machine to obtain 4.67 g of freeze-dried cell (spore) powder containing cells in an amount of $4.3\times10^9$ CFU/g.

Production Example 7

Preparation of Whole-Culture Powder of *Paenibacillus polymyxa* BS-0105

By freeze-drying 100 mL of whole culture obtained according to Production Example 2, 3.56 g of whole-culture powder containing cells in an amount of $4.1\times10^9$ CFU/g was obtained.

Formulation examples are given below. The term "parts" are by weight.

Formulation Example 1

Preparation of a Wettable Powder

About 60 parts (dry weight) of the bacterium of the present invention obtained according to each of Production Examples 4, 5, 6 and 7 was mixed with 20 parts of soybean flour, 10 parts of peptone and 10 parts of D-glucose to obtain a wettable powder containing cells.

Formulation Example 2

Preparation of a Wettable Powder

About 80 parts (dry weight) of the bacterium of the present invention obtained according to each of Production Examples 4 and 5 was mixed with 20 parts of soybean flour to obtain a wettable powder containing cells.

Formulation Example 3

Preparation of a Culture Material

A loopful of stored cells of strain BS-0105 of the present invention were inoculated into a 250-mL Erlenmeyer flask containing 50 mL of YPMG medium, and then cultured for 6 days at 30° C. and a number of shakes of 100 shakes/min. Subsequently, zeolite and soybean flour were mixed in the ratio of 9:1 and 200 g of the mixture was placed in a mayonnaise bottle, followed by adding thereto 50 ml of water, and the resulting mixture was sterilized at 121° C. for 30 minutes. To the material thus obtained was added 1 mL of the culture obtained by the pre-cultivation described above, and incubated at 30° C. for 10 days to obtain a culture material containing cells of strain BS-0105 in an amount of $10^9$ CFU/g.

The fact that the method for controlling plant diseases of the present invention has control effect on the plant diseases is demonstrated below with test examples.

Test Example 1

Test for the Control Effect of a Culture of Each Strain on Cucumber Anthracnose

Each of plastic pots was filled with horticultural compost and sown with cucumber (cultivar: Suyo), followed by growing in a greenhouse for 20 days. The cotyledon of the cucumber young seedling having a developed first true leaf was coated with 0.1 mL of whole culture of each of strains BS-0048, BS-0074, BS-0105 and BS-0277 prepared by the method described in Production Example 1. After the pots were allowed to stand in a glass house at 25° C. for 3 days, the plants were inoculated with a suspension of cucumber anthracnose fungus conidia in distilled water (*Colletotrichum orbiculare*, $1\times10^6$ spores/ml) by spraying. The pots were allowed to stand in a dark moist chamber at 25° C. for 24 hours and then in a glass house at 25° C. for 7 days to cause the disease. Lesions in the first true leaf of each seedling were counted and the protective value was calculated from the number of the lesions by the following equation to make a comparison with respect to control effect. The results are shown in Table 2.

$$\text{Protective value}=\{1-(\text{number of lesions on treated plot}/\text{number of lesions on untreated plot})\}\times100$$

TABLE 2

Table 2: Test for control effect of a culture of
each strain on cucumber anthracnose

| Strain No. | Number of lesions | Protective value |
|---|---|---|
| BS-0048 strain | 39.5 | 74.3 |
| BS-0074 strain | 31.5 | 79.5 |
| BS-0105 strain | 31.5 | 79.5 |
| BS-0277 strain | 38.5 | 74.9 |
| Acibenzolar-S-methyl 20 ppm | 5 | 96.7 |
| Untreated | 153.5 | — |

As is clear from the results shown in Table 2, when the cotyledon was treated with the culture of each bacterium of the present invention, the culture markedly controlled the infection of the first true leaf like Acibenzolar-S-methyl, a well-known controller.

Test Example 2

Test for the Control Effect of Purified Spores on Cucumber Anthracnose

Each of plastic pots was filled with horticultural compost and sown with cucumber (cultivar: 15 Suyo), followed by growing in a greenhouse for 20 days. The cucumber young seedling having a developed second true leaf was subjected to foliage application treatment with a spore preparation sample of strain BS-0105 obtained by formulating the bacterium of the present invention produced by the method described in each of Production Examples 4, 5, 6 and 7, by the method described in Formulation Example 1, so that the proportion of cells might be $2 \times 10^7$ CFU/mL. After the pots were allowed to stand in a dark moist chamber at 25° C. for 24 hours and then in a glass house at 25° C. for 4 days, the plants were inoculated with a suspension of cucumber anthracnose fungus conidia in distilled water (*Colletotrichum orbiculare*, $1 \times 10^6$ spores/ml) by spraying. The pots were allowed to stand in a dark moist chamber at 25° C. for 24 hours and then in a glass house at 25° C. for 7 days to cause the disease. Lesions in each leaf were counted and the protective value was calculated from the number of the lesions by the following equation to make a comparison with respect to control effect. The results are shown in Table 3.

Protective value={1−(number of lesions on treated plot/number of lesions on untreated plot)}×100

TABLE 3

Table 3: Control effect of BS-015 strain on cucumber anthracnose

| Treated plot | Formulation | First true leaf | | Second true leaf | |
|---|---|---|---|---|---|
| | | Number of lesions per leaf | Protective value | Number of lesions per leaf | Protective value |
| BS-0105 strain cells $2 \times 10^7$ CFU/mL | Production Example 4 | 2.5 b | 99 | 0 c | 100 |
| | Production Example 5 | 4.3 b | 98.2 | 0.5 c | 99.9 |
| | Production Example 6 | 8.5 b | 96.6 | 0 c | 100 |
| | Production Example 7 | 0 b | 100 | 0 c | 100 |
| Impression wettable powder $2 \times 10^7$ CFU/mL | — | 233 a | 5.7 | 225.7 b | 58.5 |
| Acibenzolar-S-methyl 20 ppm | — | 0 b | 100 | 5.5 c | 99 |
| Untreated | — | 247 a | | 544 a | |

In Table 3, the same alphabetic letters indicate that there was no significant difference (significance level: 0.05).

As is clear from the results shown in Table 3, all of the formulations composed mainly of the bacterium of the present invention exhibited a control effect equal or superior to that of an Impression wettable powder and Acibenzolar-S-methyl which are well-known controllers.

Test Example 3

Test for the Control Effect of Purified Spores on Cucumber Bacterial Blight

Each of plastic pots was filled with horticultural compost and sown with cucumber (cultivar: Suyo), followed by growing in a greenhouse for 20 days. The cucumber young seedling having a developed second true leaf was subjected to foliage application treatment with a spore preparation sample of strain BS-0105 obtained by formulating the bacterium of the present invention produced by the method described in Production Example 5, by the method described in Formulation Example 1, so that the proportion of cells might be $2 \times 10^7$ CFU/mL. After the pots were allowed to stand in a dark moist chamber at 25° C. for 24 hours and then in a glass house at 25° C. for 4 days, the plants were inoculated with a suspension ($1 \times 10^8$ CFU/mL) of cucumber bacterial blight bacterium (*Pseudomonas syringae* pv. *lachrymans*) in distilled water by spraying. The pots were allowed to stand in a dark moist chamber at 25° C. for 24 hours and then in a glass house at 25° C. for 7 days to cause the disease. Lesions in the second true leaf of each seedling were counted and the protective value was calculated from the number of the lesions by the following equation to make a comparison with respect to control effect. The results are shown in Table 4.

Protective value={1−(number of lesions on treated plot/number of lesions on untreated plot)}×100

TABLE 4

Table 4: Control effect of BS-0105 strain on cucumber bacterial blight

| Treated plot | Number of lesions per leaf | Protective value |
|---|---|---|
| BS-0105 strain cells $2 \times 10^7$ CFU/mL | 2.2 b | 92.6 |
| Impression wettable powder $2 \times 10^7$ CFU/mL | 50 a | 0 |

TABLE 4-continued

Table 4: Control effect of BS-0105 strain on cucumber bacterial blight

| Treated plot | Number of lesions per leaf | Protective value |
|---|---|---|
| Acibenzolar-S-methyl 20 ppm | 0 b | 100 |
| Untreated | 29.3 a | — |

In Table 4, the same alphabetic letters indicate that there was no significant difference (significance level: 0.05).

As is clear from the results shown in Table 4, the formulation composed mainly of the bacterium of the present invention exhibited a control effect equal or superior to that of an impression wettable powder and Acibenzolar-S-methyl which are well-known controllers.

Test Example 4

Test for the Control Effect of Purified Spores on Strawberry Anthracnose

Strawberry seedlings (cultivar: Akihime) cultivated in plastic pots and having about 10 developed leaflets were subjected to foliage application treatment with a spore preparation sample of strain BS-0105 obtained by formulating the bacterium of the present invention produced by the method described in Production Example 5, by the method described in Formulation Example 2, so that the proportion of cells might be $2 \times 10^7$ CFU/mL. After the pots were allowed to stand in a dark moist chamber at 25° C. for 24 hours and then in a glass house at 25° C. for 3 days (or 1 day in the case of Amister 20 flowable), the plants were inoculated with a suspension of strawberry anthracnose fungus conidia in distilled water (*Glomerella cigulata*, $2 \times 10^6$ spores/ml) by spraying. The pots were allowed to stand in a dark moist chamber at 25° C. for 24 hours and then in a glass house at 25° C. for 14 days to cause the disease. The disease severity was calculated by the following equation and the protective value was calculated from the disease severity values by the following equation to make a comparison with respect to control effect. The results are shown in Table 5.

Disease severity=(Σdisease severity index×number of pertinent seedlings/4×number of inspected seedlings)×100

Disease severity index 0: no infection; disease severity index 1: a few small spots were observed on a leaflet; disease severity index 2: a large number of small spots were observed on stalks and leaves; disease severity index 3: conspicuous large spots were present on stalks and leaves; disease severity index 4: wilt and withering into death Protective value={1−(disease severity on treated plot/disease severity on untreated plot)}×100

TABLE 5

Table 5: Control effect of BS-0105 strain on strawberry anthracnose

| Treated plot | Disease severity | Protective value |
|---|---|---|
| BS-0105 strain cells $2 \times 10^7$ CFU/mL | 1.6 b | 97.9 |
| Amister-20 flowable 100 ppm | 3.1 b | 95.8 |
| Acibenzolar-S-methyl 20 ppm | 10.9 b | 85.1 |
| Untreated | 73.4 a | — |

In Table 5, the same alphabetic letters indicate that there was no significant difference (significance level: 0.05).

As is clear from the results shown in Table 5, the formulation composed mainly of the bacterium of the present invention showed a lower disease severity and a higher control effect than did Amister 20 flowable and Acibenzolar-S-methyl which are well-known controllers.

Test Example 5

Test for the Control Effect of a Culture Broth on Melon Bacterial Blight

Each of nursery trays was filled with Aisai No. 1 (mfd. by Katakura Chikkarin Co., Ltd.) and a melon (cultivar: Arles) seedling was raised in each tray. In this case, a seed treatment plot was prepared by immersing melon seeds in a Petri dish containing 10 mL ($10^8$ spores/mL) of the culture broth of strain BS-0105 prepared in Production Example 2, followed by bacterization at 30° C. for 2 hours. After the development of a cotyledon, the seedling was potted in a 12-cm polyethylene pot filled with Aisai No. 1. When three true leaves were completely developed, the following plots were prepared: plots on which drench or foliar spray, respectively, treatment with 1 mL (108 spores/mL) of the culture broth of strain BS-0105 prepared in Production Example 2 was carried out, and a plot on which foliar spray of 2 mL of a 2 ppm solution of Acibenzolar-S-methyl was carried out. As to the inoculation of the pathogenic bacterium (*Pseudomonas syringae* pv. *lachrymans*), 5 days after the treatment, a liquid containing the bacterial blight bacterium previously cultured on a potato semisynthetic medium (a decoction consisting of 300 g of potato and 1 L of distilled water, calcium nitrate tetrahydrate 0.5 g, disodium hydrogenphosphate dodecahydrate 2 g, peptone 5 g, sucrose 20 g, powdered agar 15 g) was inoculated on the whole of each leaf by spraying so that the reverse side of the leaf might be mainly treated. Inspection for infection was carried out by counting lesions in each of leaves from second to fourth leaves 8 days after the inoculation with the pathogenic bacterium. The protective value was calculated from the number of the lesions by the following equation to make a comparison with respect to control effect. The results are shown in Table 6.

Protective value={1−(number of lesions on treated plot/number of lesions on untreated plot)}×100

TABLE 6

Table 6: Control effect of BS-0105 strain on melon bacterial blight

| | Protective value | | | |
|---|---|---|---|---|
| Treated plot | Second leaf | Third leaf | Fourth leaf | Average |
| BS-0105 strain seed treatment | 28.0 | 65.3 | 59.5 | 50.9 |

TABLE 6-continued

Table 6: Control effect of BS-0105 strain on melon bacterial blight

| Treated plot | Protective value | | | |
|---|---|---|---|---|
| | Second leaf | Third leaf | Fourth leaf | Average |
| BS-0105 strain foliar application | 100.0 | 53.1 | — | 51.0 |
| BS-0105 strain drench treatment | 100.0 | 81.3 | 88.9 | 90.0 |
| Acibenzolar-S-methyl 2 ppm | 100.0 | 68.8 | 66.7 | 78.5 |

As is clear from the results shown in Table 6, the culture of the bacterium of the present invention exhibited a control effect equal or superior to that of Acibenzolar-S-methyl, a well-known controller, when any of the seed, foliar spray and drench treatments with the aforesaid culture was carried out.

Test Example 6

Test for the Control Effect of a Culture Broth on *Fusarium wilt* of Melon

Each of nursery trays was filled with Aisai No. 1 and a melon (cultivar: Prince) seedling was raised in each tray. In this case, melon seeds had been immersed in a Petri dish containing 10 mL ($10^8$ spores/mL) of the culture broth of strain BS-0105 prepared in Production Example 2, followed by bacterization at 30° C. for 2 hours. After the development of a cotyledon, the seedling was potted in a 10.5-cm polyethylene pot filled with infected soil having *Fusarium wilt* (*Fusarium oxysporum* f. sp. *melonis*), followed by drench with the culture broth of *Bacillus* sp. BS-0105 prepared in Production Example 2, in a proportion of 1 mL/pot ($10^8$ spores/mL). In the case of Benlate wettable powder, drench treatment with 2 mL of a 1000-fold dilution (concentration: 500 ppm) of the wettable powder was carried out. The disease severity was calculated by the following equation and the protective value was calculated from the disease severity values by the following equation to make a comparison with respect to control effect. The results are shown in Table 7.

Disease severity=(Σdisease severity index×number of seedlings/4×number of seedlings)×100

Disease severity index: rated in the following scale of zero to four; 0 (healthy), 1 (mild), 2 (moderate), 3 (serious) and 4 (withering into death)

Protective value={1−(disease severity on each treated plot/disease severity on untreated plot)}×100

TABLE 7

Table 7: Control effect of BS-0105 strain on Fusarium wilt of melon

| Treated plot | Percentage of infected seedlings | Disease severity | Protective value |
|---|---|---|---|
| BS-0105 strain + drench | 40 | 25 | 61.5 |
| Benlate wettable powder 500 ppm | 20 | 5 | 92.3 |
| Untreated | 80 | 65 | — |

As is clear from the results shown in Table 7, the culture of the bacterium of the present invention exhibited a control effect equal to that of Benlate wettable powder, a well-known controller, when used for the seed and drench treatments.

The following examples are given as methods for obtaining compound 1 (Fusaricidin A) and compound 2 (Fusaricidin B) from a culture of *Paenibacillus* sp. BS-0048, *Paenibacillus* sp. BS-0074, *Paenibacillus polymyxa* BS-0105 or *Paenibacillus* sp. BS-0277.

Cultivation Example 1

Cultivation of *Paenibacillus polymyxa* BS-0105

A loopful of stored cells of strain BS-0105 of the present invention were inoculated into a 100-mL Erlenmeyer flask containing 10 mL of YPMG medium (D-glucose 10 g, meat extract 1 g, yeast extract 3 g, peptone 5 g, distilled water 1 L, pH 7.0) and then cultured for 3 days in the dark at 25° C. and a number of revolutions of 200 rpm. A 100-mL Erlenmeyer flask containing 10 mL of a production medium (D-glucose 20 g, soybean flour 10 g, corn steep liquor 5 g, glycerol 2.5 g, corn starch 2.5 g, yeast extract 1 g, NaCl 1 g, $CaCO_3$ 1 g, distilled water 1 L, pH 7.0) was inoculated with 0.5 mL of the culture obtained by the pre-cultivation described above, followed by shaking culture for 4 days at 25° C. and a number of revolutions of 200 rpm Extraction Example 1

Extraction from a Culture Broth of *Paenibacillus polymyxa* BS-0105

After 300 ml of the culture broth was extracted overnight by shaking with an equal volume of butanol, the resulting butanol extract solution was concentrated in a rotary evaporator. The extract was extracted with ethyl acetate/distilled water and then the aqueous layer was extracted with butanol/distilled water. The butanol layer was recovered and then concentrated to dryness.

Purification Example 1

Purification of a Mixture of Compound 1 (Fusaricidin A) and Compound 2 (Fusaricidin B)

The crude extract was dissolved in 4 mL of dimethyl sulfoxide and purified by HPLC. The HPLC conditions were as follows. That is, using acetonitrile-0.1% (v/v) TFA (35:65) as a mobile phase and a Senshu Pak PEGASIL ODS2 20×250 mm as a column, HPLC separation was carried out under the following conditions: injecting volume for one run 0.1 ml, column temperature 40° C. and flow rate 9 mL/min. A component at a retention time of 23 minutes was recovered and then concentrated to dryness to obtain 60.7 mg of a mixture containing compound 1 and compound 2 in the ratio of 3:2.

Identification of Compound 1 (Fusaricidin A) and Compound 2 (Fusaricidin B)

The mixture containing compound 1 and compound 2 in the ratio of 3:2 was dissolved in $DMSO-D_6$, followed by $^{13}C$-NMR measurement. As a result, it was found that the thus obtained $^{13}C$-NMR measured values agreed with those for Fusaricidin A and Fusaricidin B described in non-patent documents 4 and 5. Table 8 shows chemical shift data for compound 1 (Fusaricidin A) and compound 2 (Fusaricidin B).

TABLE 8

Table 8: Chemical shift data for Compound 1
(Fusaricidin A) and Compound 2 (Fusaricidin B)

| Fusaricidin A | | | Fusaricidin B | | |
|---|---|---|---|---|---|
| Moiety | Position | $\delta_c$ | Moiety | Position | $\delta_c$ |
| L-Thr(1) | 1 | 56.7 | L-Thr(1) | 1 | 56.7 |
| | 2 | 70.3 | | 2 | 70.1 |
| | 3 | 16.2 | | 3 | 16.5 |
| | 4 | 168.4 | | 4 | 168.1 |
| D-Val(1) | 5 | 57.0 | D-Val(1) | 5 | 56.9 |
| | 6 | 31.5 | | 6 | 31.5 |
| | 7 | 18.2 | | 7 | 17.9 |
| | 8 | 19.0 | | 8 | 19.0 |
| | 9 | 170.8 | | 9 | 171.0 |
| L-Val(2) | 10 | 57.8 | L-Val(2) | 10 | 58.5 |
| | 11 | 30.1 | | 11 | 29.6 |
| | 12 | 18.0 | | 12 | 18.2 |
| | 13 | 19.2 | | 13 | 19.9 |
| | 14 | 172.9 | | 14 | 172.3 |
| D-allo-Thr (2) | 15 | 60.2 | D-allo-Thr (2) | 15 | 59.5 |
| | 16 | 65.6 | | 16 | 65.6 |
| | 17 | 19.5 | | 17 | 19.7 |
| | 18 | 170.3 | | 18 | 170.3 |
| D-Asn | 19 | 50.4 | D-Gln | 19 | 52.7 |
| | 20 | 36.5 | | 20 | 26.1 |
| | 21 | 172.4 | | 21 | 31.8 |
| | 22 | 169.6 | | 22 | 174.3 |
| | | | | 23 | 170.5 |
| D-Ala | 23 | 47.7 | D-Ala | 24 | 47.8 |
| | 24 | 17.2 | | 25 | 17.2 |
| | 25 | 170.5 | | 26 | 170.5 |
| GHPD | 26 | 171.9 | GHPD | 27 | 17.20 |
| | 27 | 43.0 | | 28 | 43.3 |
| | 28 | 67.5 | | 29 | 67.5 |
| | 29 | 36.7 | | 30 | 36.7 |
| | 30 | 25.2 | | 31 | 25.2 |
| | 31-37 | 28.6 | | 32-38 | 28.6 |
| | | 29.0 | | | 29.0 |
| | | 29.1 | | | 29.0 |
| | 38 | 26.0 | | 39 | 26.0 |
| | 39 | 28.4 | | 40 | 28.4 |
| | 40 | 40.7 | | 41 | 40.7 |
| | 41 | 156.7 | | 42 | 156.7 |

GHPD: 15-guanidino-3-hydroxypentadecanoic acid

Purification Example 2

Production of Compound 1 (Fusaricidin A) and Compound 2 (Fusaricidin B) from *Paenibacillus* sp. BS-0048, *Paenibacillus* sp. BS-0074 and *Paenibacillus* sp. BS-0277

Strains BS-0048, BS-0074, BS-0105 and BS-0277 were cultured according to the above-mentioned Culture Example 1. After 10 ml of the thus obtained culture broth of each strain was extracted overnight by shaking with an equal volume of butanol, the resulting butanol extract solution was concentrated in a rotary evaporator. The extract was dissolved in 1 mL of dimethyl sulfoxide, followed by LC/MS analysis (LC and MS analyzers are NANOSPACE SI-2 (Shiseido) and FINIGAN LCQ$^{DUO}$ (Thermo Quest)). As to the HPLC analysis conditions, using a 27% aqueous acetonitrile solution containing 0.1% TFA (trifluoroacetic acid) as a mobile phase and CAPCELL PAK $C_{18}$ UG120 3 μm 2.0×100 mm (Shiseido) as a column, separation was carried out at an injecting volume for one run of 3 μL, a column temperature of 40° C. and a flow rate 0.2 mL/min., and then molecular weight measurement was carried out under the following conditions. That is, the measurement was carried out under conditions of a capillary temperature of 245° C., a capillary voltage of 10 V, a sheath gas flow rate of 95 arb, an auxiliary gas flow rate of 10 arb, a spray voltage of 5 kV and an electron multiplier voltage of 700 V. As a result, a molecular ion peak corresponding to a molecular weight of 883 $(M+H)^+$ was detected at a retention time of 18.5 minutes and a molecular ion peak corresponding to a molecular weight of 897 $(M+H)^+$ at a retention time of 17.8 minutes, in the case of the culture extract of any of strains BS-0048, BS-0074, BS-0105 and BS-0277. Also in the case of the mixture of compound 1 and compound 2 described in Purification Example 1, the same molecular ion peaks as above were detected at the same retention times, respectively, as above. By these results and the result of the above-mentioned $^{13}$C-NMR measurement, it was confirmed that the substance detected at a retention time of 18.5 minutes was Fusaricidin A and the substance detected at a retention time of 17.8 minutes Fusaricidin B.

Preparation Example 1

Preparation of a Soluble Concentrate

The mixture of compound 1 and compound 2 in the ratio of 3:2 was dissolved in dimethyl sulfoxide and the resulting solution was diluted to a target concentration with distilled water.

Evaluation Example 1

Evaluation of an Activity of Inducing Resistance to Plant Diseases

Siegrist, J. et al. (Physiological and Molecular Plant Pathology 53, 223-238:1998) have revealed the improvement of elicitor responsiveness by Acibenzolar-S-methyl, a substance capable of inducing resistance to plant diseases, by adopting a method in which the elicitor responsiveness of parsley cultured cells is measured by the detection of phytoalexin using fluorescence, in a model experimental system for investigating an activity of inducing disease resistance in plant. The activity of inducing disease resistance in plant of compound 1 and compound 2 according to the present invention was also evaluated according to the method of Siegrist, J. et al. The results are shown in Table 9.

TABLE 9

Table 9: Results of phytoalexin detection

| Elicitor treatment | Compound-treated plot | Concentration (μM) | Relative fluorescence |
|---|---|---|---|
| Yes | Compound 1 + compound 2 (3:2) | 0.1 + 0.07 | 995.1 |
| | Acibenzolar-S-methyl | 2.5 | 754.3 |
| | Untreated-1 | — | 409.8 |
| No | Compound 1 + compound 2 (3:2) | 0.1 + 0.07 | 104.6 |
| | Acibenzolar-S-methyl | 2.5 | NT |
| | Untreated-2 | — | 87.5 |

NT: Untreated

From the results shown in Table 9, it became clear that compound 1 and compound 2 improve the elicitor responsiveness of parsley cultured cells like the existing substance having an activity of inducing disease resistance in plant and hence have an activity of inducing disease resistance in plant.

Evaluation Example 2

Test for Antimicrobial Activity Against Cucumber Bacterial Blight Bacterium

Whether compound 1 and compound 2 exhibited direct antimicrobial activity against cucumber bacterial blight bacterium (*Pseudomonas syringae* pv. *lachrymans*) was investigated. That is, cucumber bacterial blight bacterium was mixed with a potato semisynthetic medium (a decoction consisting of 300 g of potato and 1 L of distilled water, calcium nitrate tetrahydrate 0.5 g, disodium hydrogenphosphate dodecahydrate 2 g, peptone 5 g, sucrose 20 g, powdered agar 15 g) maintained at 45° C., in a proportion of $1\times10^8$ CFU/mL, and the resulting mixture was dispensed in 20 mL aliquots into sterilized Petri dishes. After the solidification of the medium, 50 µL of a solution obtained by dissolving a 3:2 mixture of compounds 1 and 2 in dimethyl sulfoxide to a concentration of 100 µg/mL was infiltrated into a paper disc with a diameter of 8 mm, and then the paper disc was allowed to stand on the medium. After 48 hours of cultivation at 25° C. in the dark, the activity was evaluated on the basis of the presence of an inhibition zone around the periphery

TABLE 10

Table 10: Direct antimicrobial activity against cucumber bacterial blight bacterium

| Compound-treated plot | Concentration (ppm) | Presence of inhibition zone |
|---|---|---|
| Compound 1 + compound 2 (3:2) | 60 + 40 | No |
| Dimethyl sulfoxide | — | No |

From the results shown in Table 10, it became clear that compound 1 and compound 2 do not exhibit direct antimicrobial activity against cucumber bacterial blight bacterium.

Evaluation Example 3

Test for Control Effect on Cucumber Bacterial Blight

Each of plastic pots was filled with horticultural compost and sown with cucumber (cultivar: Suyo), followed by growing in a greenhouse for 20 days. The cucumber young seedling having a developed second true leaf was subjected to plant foot drench treatment with the formulation obtained in the above-mentioned preparation example, in a proportion of 5 mL per seedling. After the pots were allowed to stand in a glass house at 25° C. for 3 days, the plants were inoculated with a suspension ($1\times10^8$ CFU/mL) of cucumber bacterial blight bacterium (*Pseudomonas syringae* pv. *lachrymans*) in distilled water by spraying. The pots were allowed to stand in a dark moist chamber at 25° C. for 24 hours and then in a glass house at 25° C. for 7 days to cause the disease. Lesions in each leaf were counted and the protective value was calculated from the number of the lesions by the following equation to make a comparison with respect to control effect. The results are shown in Table 11.

Protective value={1−(number of lesions on treated plot/number of lesions on untreated plot)}×100

TABLE 11

Table 11: Control effect of compound 1 and compound 2 on cucumber bacterial blight

| Treated plot | Concentration (ppm) | Number of lesions per leaf | Protective value |
|---|---|---|---|
| Compound 1 + compound 2 (3:2) | 12 + 8<br>60 + 40 | 223.8 b<br>293 b | 65.5<br>54.9 |
| Acibenzolar-S-methyl | 20 | 137.8 b | 78.8 |
| Untreated | — | 649.7 a | — |

In Table 11, the same alphabetic letters indicate that there was no significant difference (significance level: 0.05).

As is clear from the results shown in Table 11, the formulation composed mainly of compound 1 and compound 2 according to the present invention exhibited an excellent control effect on cucumber bacterial blight against which the formulation did not exhibit direct antimicrobial activity.

Evaluation Example 4

Test for Antimicrobial Activity Against *Fusarium wilt* of Cucumber

Whether compound 1 and compound 2 exhibited direct antimicrobial activity against *Fusarium wilt* of cucumber fungus (*Fusarium oxysporum* f. sp. *cucumerium*) was investigated. That is, conidia of *Fusarium wilt* of cucumber fungus was mixed with a potato•dextrose agar medium (Nissui Pharmaceutical) maintained at 45° C., in a proportion of $1\times10^7$ spores/mL, and the resulting mixture was dispensed in 20 mL aliquots into sterilized Petri dishes. After the solidification of the medium, 50 µL of a solution obtained by dissolving a 3:2 mixture of compounds 1 and 2 in dimethyl sulfoxide to each of predetermined concentrations was infiltrated into a paper disc with a diameter of 8 mm, and then the paper disc was allowed to stand on the medium. After 48 hours of cultivation at 25° C. in the dark, the activity was evaluated on the basis of the presence of an inhibition zone around the periphery of the paper disc. The results are shown in Table 12.

TABLE 12

Table 12: Direct microbial activity against Fusarium wilt of cucumber fungus

| Treated plot | Concentration (ppm) | |
|---|---|---|
| | 12 + 8 | 30 + 20 |
| Compound 1 + compound 2 (3:2) | — | — |
| Untreated | — | |

+: a clear inhibition zone was present,
—: no inhibition zone was present.

As is clear from the results shown in Table 12, the 3:2 mixture of compound 1 and compound 2 did not exhibit antimicrobial activity against *Fusarium wilt* of cucumber fungus (*Fusarium oxysporum* f. sp. *cucumerium*) even when the compounds 1 and 2 were mixed so that their concentrations might be 30 ppm and 20 ppm, respectively.

Evaluation Example 5

Test for Control Effect on *Fusarium wilt* of Cucumber

Each of plastic vats was filled with horticultural compost and sown with cucumber (cultivar: Sagamihanjiro), followed by growing in a greenhouse for 12 days. The cucumber young seedling having a developed cotyledon was subjected to foliar spray treatment with the formulation obtained in the above-mentioned preparation example, in a proportion of 1 mL per seedling. After the vats were allowed to stand in a glass house at 25° C. for 3 days, the plant foot of each plant was inoculated with 2 mL of a suspension ($3 \times 10^7$ spores/mL) of conidia of *Fusarium wilt* of cucumber fungus (*Fusarium oxysporum* f. sp. *cucumerium*) in distilled water by drench. The vats were allowed to stand in a glass house at 25° C. for 14 days to cause the disease. The disease severity was calculated from the degree of infection and then the protective value was calculated from the disease severity values by the following equation to make a comparison with respect to control effect. The results are shown in Table 13.

Disease severity=(Σdisease severity index×number of pertinent seedlings/4×number of inspected seedlings)×100

Disease severity index 0: no infection; disease severity index 1: slight yellowing in a portion close to the ground; disease severity index 2: conspicuous browning in a portion close to the ground; disease severity index 3: considerably conspicuous browning in stems and unsatisfactory growth in the above-ground part; disease severity index 4: untreatable wilt and withering into death of the plant.

Protective value={1−(disease severity on treated plot/disease severity on untreated plot)}×100

TABLE 13

Table 13: Control effect on Fusarium wilt of cucumber

| Treated plot | Concentration (ppm) | Treatment method | Disease severity | Protective value |
|---|---|---|---|---|
| Compound 1 + compound 2 (3:2) | 12 + 8 | Spray | 11.5 b | 70.2 |
| Acibenzolar-S-methyl | 20 | Spray | 9.4 b | 75.6 |
| Benlate wettable powder | 200 | Plant foot drench | 15.6 b | 59.4 |
| Untreated/fungus inoculation | — | — | 38.5 a | — |
| Untreated/no fungus inoculation | — | — | 0 | — |

In Table 13, the same alphabetic letters indicate that there was no significant difference (significance level: 0.05).

As is clear from the results shown in Table 13, the formulation composed mainly of compound 1 and 5 compound 2 according to the present invention controlled *Fusarium wilt* of cucumber, a soil disease in the case of the spray treatment on the above-ground part. The formulation exhibited an excellent control effect in the case of the treatment with a mixture of compound 1 and compound 2 in concentrations of 12 ppm and 8 ppm, respectively, which were concentrations at which the formulation did not exhibit direct antimicrobial activity.

Purification Example 3

Separation and Purification of Compound 1 (Fusaricidin A) and Compound 2 (Fusaricidin B)

In 3 mL of dimethyl sulfoxide was dissolved 133.7 mg of a mixture of compound 1 and compound 2, and these compounds were purified by HPLC. The HPLC conditions were as follows. That is, using acetonitrile-0.1% (v/v) TFA (29:71) as a mobile phase and Shiseido CAPCELL PAK $C_{18}$ SG120 5 μm 4.6×250 mm as a column, HPLC separation was carried out under the following conditions: injecting volume for one run 0.25 mL, column temperature 40° C., and flow rate 1 mL/min. Eluates at retention times of 20 minutes to 35 minutes were recovered at intervals of 30 seconds and each fraction was analyzed by LC/MS. The HPLC analysis conditions were as follows. That is, using TFA (0.1%)—containing acetonitrile—0.1% (v/v) TFA (27:73) as a mobile phase and Shiseido CAPCELL PAK $C_{18}$ UG120 3 μm 2.0×100 mm as a column, separation was carried out at an injecting volume for one run of 0.01 mL, a column temperature of 40° C. and a flow rate 0.2 mL/min., and then molecular weight measurement was carried out under the following conditions. That is, the measurement was carried out under conditions of a capillary temperature of 245° C., a capillary voltage of 10 V, a sheath gas flow rate of 95 arb, an auxiliary gas flow rate of 10 arb, a spray voltage of 5 kV and an electron multiplier voltage of 700 V.

Fractions containing compound 1 were combined and then concentrated to dryness to obtain 44.7 mg of compound 1. Fractions containing compound 2 were combined and then concentrated to dryness to obtain 24.8 mg of compound 2.

Evaluation Example 6

Evaluation of the Activity of Inducing Disease Resistance in Plant of each of Compound 1 and Compound 2

The activity of inducing disease resistance in plant of each of compound 1 and compound 2 was evaluated in the same manner as in Evaluation Example 1 by adopting the method practiced in Evaluation Example 1, i.e., the method in which the elicitor responsiveness of parsley cultured cells was measured by the detection of phytoalexin using fluorescence. The results are shown in Table 14.

TABLE 14

Table 14: Results of phytoalexin detection

| Elicitor treatment | Compound-treated plot | Concentration (μM) | Relative fluorescence |
|---|---|---|---|
| Yes | Compound 1 | 0.5 | 1000 |
| | Compound 2 | 0.5 | 1000 |
| | Acibenzolar-S-methyl | 2.5 | 664.8 |
| | untreated-1 | — | 366.2 |
| No | Compound 1 | 0.5 | 98.5 |
| | Compound 2 | 0.5 | 100.7 |
| | Acibenzolar-S-methyl | 2.5 | 86.9 |
| | untreated-2 | — | 84.7 |

From the results shown in Table 14, it became clear that each of compound 1 and compound 2 improves the elicitor responsiveness of parsley cultured cells like the existing substance having an activity of inducing disease resistance in plant and hence has an activity of inducing resistance to plant disease.

Cultivation Example 2

Cultivation of *Paenibacillus polymyxa* BS-0105

A 400-mL flask containing 100 mL of YPMG medium (D-glucose 10 g, meat extract 1 g, yeast extract 3 g, peptone 5 g, distilled water 1 L, pH 7.0) was inoculated with 100 μL of a cell suspension stored by freezing of strain BS-0105 of the present invention, followed by cultivation for 1 day at 25° C. and a number of revolutions of 210 rpm. Into a jar fermentor containing 20 L of a production medium (D-glucose 200 g, starch 600 g, ammonium sulfate 50 g, soybean flour 50 g, potassium dihydrogenphosphate 10 g, sodium chloride 5 g, magnesium sulfate 5 g, calcium carbonate 120 g) was transferred and inoculated 200 mL of the culture obtained by the pre-cultivation described above, followed by cultivation for 3 days at 25° C., an aeration rate of 10 L/min and a number of revolutions of 400 rpm.

Extraction Example 2

Extraction of Compound 3 and Compound 4

To 5 L of the culture broth obtained in the above Cultivation Example 2 were added 5 L of isopropyl alcohol and 1 L of 1 mol/L calcium chloride and the resulting mixture was filtered to obtain about 10 L of an extract solution. After 5 L of the extract solution was concentrated to 500 mL, the concentrate CAPCELL PAK $C_{18}$ UG120 3 μm 2.0×100 mm), and fractions corresponding to each of 954 m/z[M+H]$^+$ and 968 m/z [M+H]$^+$ were combined and concentrated to dryness to obtain 14 mg of compound 3 and 3.1 mg of compound 4.

Physicochemical Properties of Compound 3

Molecular weight: 954.16

Molecular formula: $C_{44}H_{79}N_{11}O_{12}$

Solubility: readily soluble in methanol, butanol, isopropyl alcohol and dimethyl sulfoxide; and insoluble in ethyl acetate, chloroform and hexane.

Acid hydrolysis: when hydrolyzed with 6-normal hydrochloric acid at 110° C. for 24 hours, compound 3 gave aspartic acid, valine, threonine, allothreonine and alanine in the molar ratio of 1:2:1:1:2.

Proton nuclear magnetic resonance spectrum: shown in FIG. 1.

C-13 nuclear magnetic resonance spectrum: shown in Table 15.

From the above-mentioned physicochemical properties and spectral analysis results, the chemical structure of novel compound 3 was identified as follows:

[Formula 5]

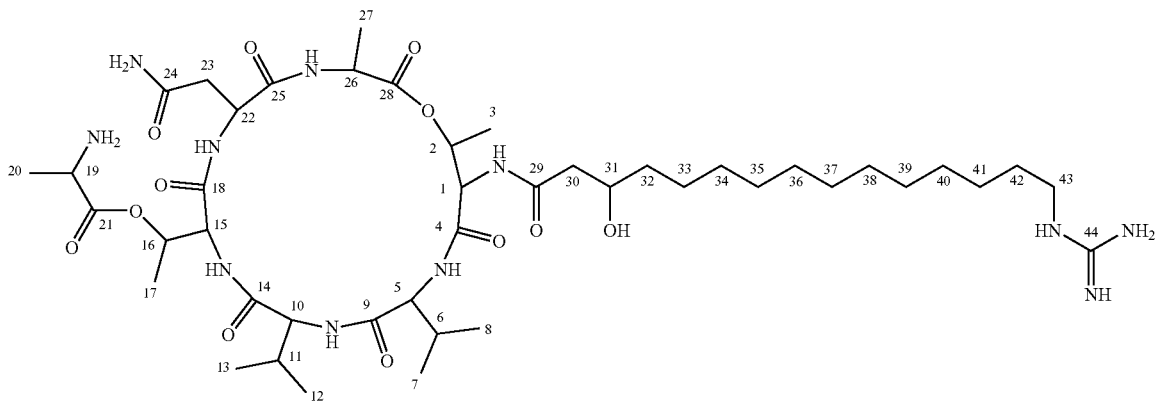

was extracted with 500 mL of butanol and the butanol layer was extracted three times with 200 mL of distilled water to obtain 600 mL of an aqueous layer. The aqueous layer was concentrated in a rotary evaporator and the resulting aqueous layer was charged into an octadecyl silica gel column. The column was washed with water, followed by elution with 10 to 25% aqueous acetonitrile solutions. The eluate was concentrated to obtain a crude extract.

Purification Example 4

Separation and Purification of Compound 3 and Compound 4

The crude extract obtained in the above Extraction Example 2 was dissolved in 4 mL of 50% methanol and purified by HPLC. The HPLC conditions were as follows. That is, using acetonitrile: 0.1% (v/v) TFA (32:68) as a mobile phase and Inertsil ODS 20×250 mm as a column, HPLC separation was carried out under the following conditions: injecting volume for one run 1.5 mL, column temperature 30° C., and flow rate 10 mL/min. Each fraction was analyzed by LC/MS (mobile phase: TFA (0.1%)—containing acetonitrile—0.1% (v/v) TFA (27:73), column: Shiseido Physicochemical Properties of Compound 4

Molecular weight: 968.19

Molecular formula: $C_{45}H_{81}N_{11}O_{12}$

Solubility: readily soluble in methanol, butanol, isopropyl alcohol and dimethyl sulfoxide; and insoluble in ethyl acetate, chloroform and hexane.

Acid hydrolysis: when hydrolyzed with 6-normal hycrochloric acid at 110° C. for 24 hours, compound 4 gave glutamic acid, valine, threonine, allothreonine and alanine in the molar ratio of 1:2:1:1:2.

Figure 2:
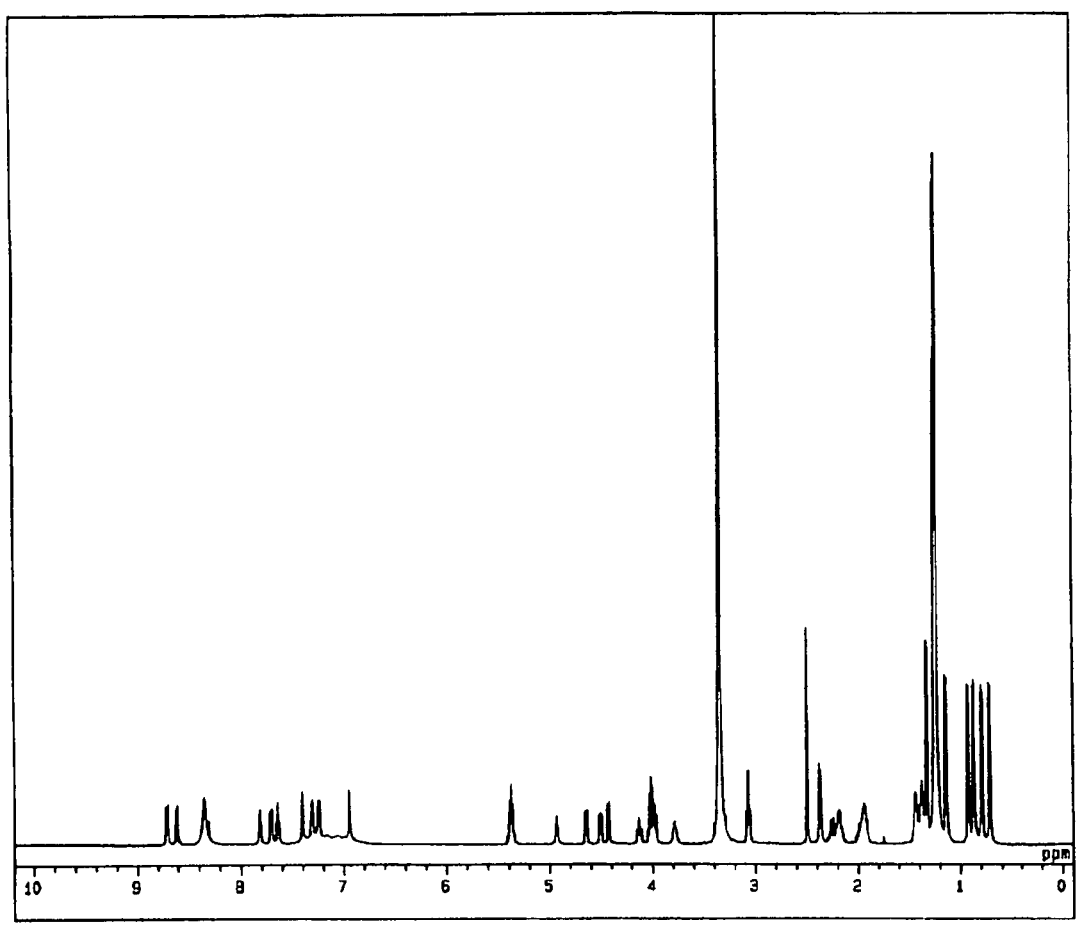
FIG. 2 A proton nuclear magnetic resonance spectrum (DMSO-d6) of the novel compound 4 of the present invention.

Proton nuclear magnetic resonance spectrum (DMSO-d6): shown in FIG. 2.

C-13 nuclear magnetic resonance spectrum (DMSO-d6): shown in Table 15.

From the above-mentioned physicochemical properties and spectral analysis results, the chemical structure of novel compound 4 was identified as follows:

[Formula 6]

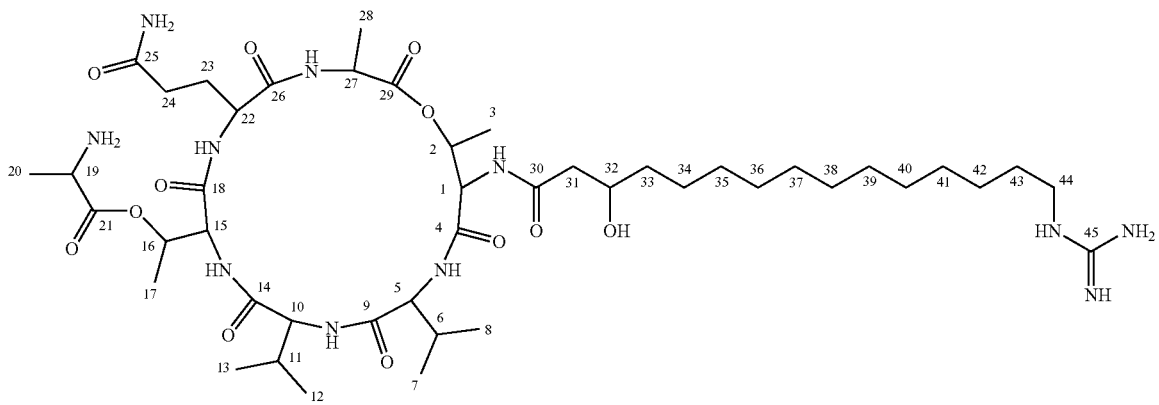

TABLE 15

Table 15: C-13 nuclear magnetic resonance chemical shift data for compound 3 and compound 4

| Compound 3 | | | Compound 4 | | |
|---|---|---|---|---|---|
| Moiety | Position | $\delta_c$ | Moiety | Position | $\delta_c$ |
| Thr(1) | 1 | 56.7 | Thr(1) | 1 | 56.3 |
| | 2 | 70.1 | | 2 | 69.7 |
| | 3 | 16.5 | | 3 | 16.4 |
| | 4 | 168.2 | | 4 | 167.7 |
| Val(1) | 5 | 56.9 | Val(1) | 5 | 56.3 |
| | 6 | 31.7 | | 6 | 32.2 |
| | 7 | 18.2 | | 7 | 17.2 |
| | 8 | 19.1 | | 8 | 19.0 |
| | 9 | 170.9 | | 9 | 171.5 |
| Val(2) | 10 | 58.1 | Val(2) | 10 | 59.9 |
| | 11 | 29.9 | | 11 | 28.7 |
| | 12 | 17.9 | | 12 | 19.0 |
| | 13 | 19.2 | | 13 | 19.1 |
| | 14 | 172.5 | | 14 | 172.5 |
| allo-Thr(2) | 15 | 56.3 | allo-Thr(2) | 15 | 55.3 |
| | 16 | 70.8 | | 16 | 70.8 |
| | 17 | 15.5 | | 17 | 15.1 |
| | 18 | 168.6 | | 18 | 168.4 |
| Ala(1) | 19 | 47.9 | Ala(1) | 19 | 47.9 |
| | 20 | 15.6 | | 20 | 15.4 |
| | 21 | 169.3 | | 21 | 169.4 |
| Asn | 22 | 50.2 | Gln | 22 | 51.9 |
| | 23 | 36.3 | | 23 | 26.9 |
| | 24 | 172.3 | | 24 | 32.0 |
| | 25 | 169.7 | | 25 | 174.4 |
| | | | | 26 | 170.0 |
| Ala(2) | 26 | 48.0 | Ala(2) | 27 | 48.5 |
| | 27 | 17.5 | | 28 | 16.9 |
| | 28 | 170.5 | | 29 | 170.8 |
| GHPD | 29 | 172.0 | GHPD | 30 | 172.1 |
| | 30 | 43.1 | | 31 | 43.4 |
| | 31 | 67.5 | | 32 | 67.6 |
| | 32 | 36.8 | | 33 | 36.8 |
| | 33 | 25.2 | | 34 | 25.3 |
| | 33-39 | 29.0-29.1 | | 35-40 | 29.0-29.1 |
| | 40 | 28.6 | | 41 | 28.6 |
| | 41 | 26.0 | | 42 | 26.0 |
| | 42 | 28.4 | | 43 | 28.4 |
| | 43 | 40.7 | | 44 | 40.7 |
| | 44 | 156.7 | | 45 | 156.8 |

GHPD: 15-guanidino-3-hydroxypentadecanoic acid

Evaluation Example 7

Evaluation of the Activity of Inducing Disease Resistance in Plant of each of Compound 3 and Compound 4

The activity of inducing resistance to plant diseases of each of compound 3 and compound 4 was evaluated in the same manner as in Evaluation Example 1 by adopting the method practiced in Evaluation Example 1, i.e., the method in which the elicitor responsiveness of parsley cultured cells was measured by the detection of phytoalexin using fluorescence. The results are shown in Table 16.

TABLE 16

Table 16: Results of phytoalexin detection

| Elicitor | Compound-treated plot | Concentration (μM) | Relative fluorescence |
|---|---|---|---|
| Yes | Compound 3 | 0.5 | 222.7 |
| | Compound 4 | 0.5 | 504.8 |
| | Acibenzolar-S-methyl | 2.5 | 377.5 |
| | Untreated-1 | — | 135.3 |
| No | Compound 3 | 0.5 | 3.1 |
| | Compound 4 | 0.5 | 0.7 |
| | Acibenzolar-S-methyl | 2.5 | 0.8 |
| | Untreated-2 | — | 1.0 |

From the results shown in Table 16, it became clear that compound 3 and compound 4 improve the elicitor responsiveness of parsley cultured cells like the existing substance having an activity of inducing resistance to plant disease and hence have an activity of inducing disease resistance in plant.

INDUSTRIAL APPLICABILITY

As described above in detail, the strains of the genus *Paenibacillus* of the present invention, such as novel *Paenibacillus* sp. BS-0048, *Paenibacillus* sp. BS-0074, *Paenibacillus polymyxa* BS-0105 and *Paenibacillus* sp. BS-0277 are very effective in controlling various plant diseases and hence are useful as controllers. Moreover, it has become clear that these strains of the genus *Paenibacillus*, compound 1 (Fusaricidin A) and compound 2 (Fusaricidin B), which are well-known substances, and novel compounds 3 and 4 have an activity of inducing resistance to plant diseases and exhibit control effect also on plant diseases which have been considered uncontrollable. Furthermore, it has been revealed that since these strains of the genus *Paenibacillus* and these compounds have an activity of inducing disease resistance in plant, they can protect plants from infections with plant pathogens.

The invention claimed is:

1. An isolated strain belonging to the genus *Paenibacillus* which is *Paenibacillus polymyxa* BS-0105 having accession number IPOD FERM BP-10379.

2. The strain belonging to the genus *Paenibacillus* according to claim 1 that can produce at least one compound selected from compound 3 and compound 4 which have the following structures:

[Formula 3]

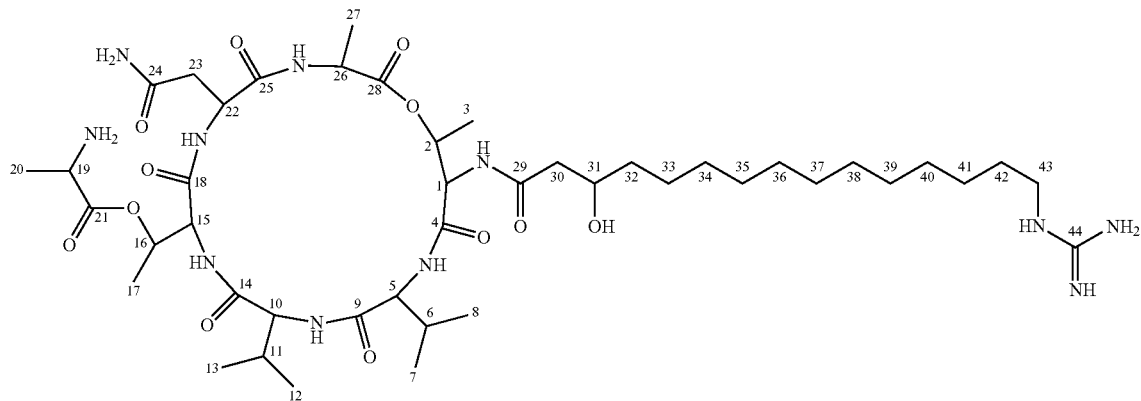

Compound 3

[Formula 2]

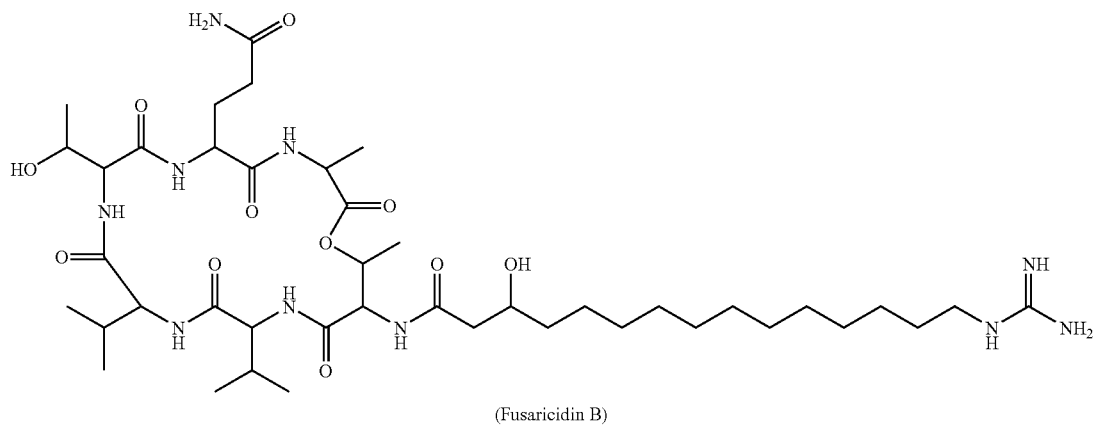

Compound 2

(Fusaricidin B)

[Formula 4]

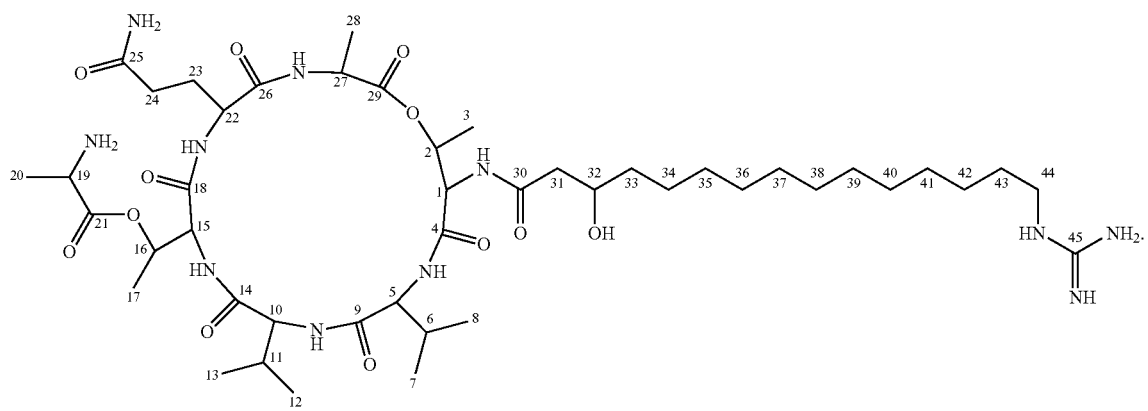

Compound 4

3. The strain belonging to the genus *Paenibacillus* according to claim 2, which can control plant diseases caused by Gram-negative bacteria, by inducing disease resistance in plants.

4. The strain belonging to the genus *Paenibacillus* according to claim 2, which can control plant diseases caused by strains belonging to the genus *Fusarium*, by inducing disease resistance in plants.

5. A composition comprising a strain belonging to the genus *Paenibacillus* according to claim 1, wherein the composition comprises a carrier and an amount of said strain effective to control plant disease.

6. The composition according to claim 5, which comprises spores, vegetative cells or whole culture of the strain belonging to the genus *Paenibacillus*.

7. The composition according to claim 5, which controls plant diseases caused by strains belonging to the genus *Colletotrichum* or strains belonging to the genus *Glomerella*.

8. The composition according to claim 5, which controls anthracnose of plants of the Cucurbitaceae or strawberry anthracnose.

9. The composition according to claim 5, which controls bacterial blight of plants of the Cucurbitaceae caused by strains belonging to the genus *Pseudomonas*, by exhibiting an activity of inducing disease resistance in plants.

10. The composition according to claim 5, used for foliage, rooting zone and/or seed treatment.

11. A method of controlling plant diseases, characterized by applying a strain belonging to the genus *Paenibacillus* according to claim 1.

12. A method of controlling plant diseases according to claim 11, wherein the strain belonging to the genus *Paenibacillus* exhibits an activity of inducing disease resistance in plants, to protect the plant from infections with plant pathogens.

13. A method of controlling plant diseases according to claim 12, wherein the strain belonging to the genus *Paenibacillus* exhibits an activity of inducing disease resistance in plants, without exhibiting direct microbial activity, and as a result, controls the plant diseases.

* * * * *